(12) United States Patent
Starr et al.

(10) Patent No.: US 6,849,049 B2
(45) Date of Patent: Feb. 1, 2005

(54) PATIENT MONITOR AND METHOD OF USING SAME

(75) Inventors: Eric W. Starr, Allison Park, PA (US); Michael T. Kane, Delmont, PA (US); Eugene N. Scarberry, Trafford, PA (US)

(73) Assignee: RIC Investments, Inc., Wilmington, DE (US)

(*) Notice: Subject to any disclaimer, the term of this patent is extended or adjusted under 35 U.S.C. 154(b) by 0 days.

(21) Appl. No.: 10/372,381

(22) Filed: Feb. 21, 2003

(65) Prior Publication Data

US 2003/0130591 A1 Jul. 10, 2003

Related U.S. Application Data

(63) Continuation of application No. 09/961,618, filed on Sep. 24, 2001, now Pat. No. 6,544,192, which is a continuation-in-part of application No. 09/438,081, filed on Nov. 10, 1999, now Pat. No. 6,342,040, which is a continuation of application No. 09/030,221, filed on Feb. 25, 1998, now Pat. No. 6,017,315.

(51) Int. Cl.[7] .............. A61B 5/08; A62B 7/00; A62B 9/02; A62B 18/02
(52) U.S. Cl. ............. 600/538; 600/529; 128/204.18; 128/204.22; 128/205.25; 128/205.24; 128/206.21
(58) Field of Search ............... 600/529, 531–533, 600/537, 538; 128/200.24, 204.18, 204.21, 204.22, 204.29, 205.24, 205.25, 206.21

(56) References Cited

U.S. PATENT DOCUMENTS

| | | |
|---|---|---|
| 3,924,612 A | 12/1975 | Dempster et al. |
| 4,083,245 A | 4/1978 | Osborn |
| 4,170,228 A | 10/1979 | Elson et al. |

(List continued on next page.)

FOREIGN PATENT DOCUMENTS

| | | |
|---|---|---|
| EP | 0 086 259 A2 | 8/1983 |
| EP | 0 772 026 A2 | 5/1997 |
| JP | 60-168433 | 8/1985 |
| JP | 63-99841 | 5/1988 |
| JP | 3-39140 | 2/1991 |
| WO | WO 97/18752 | 5/1997 |

OTHER PUBLICATIONS

Quinn et al., "The Differentiation of Snoring Mechanisms Using Sound Analysis", Clin. Otolaryngol. 1996; vol. 21, 119–123. iz et al., "Acoustic Analysis of Snoring Sound in Patients With Simple Snoring and Obstructive Sleep Apnea," Eur Respir J., 1996; vol. 9, 2365–2370.
Keyhani et al., "Numerical Stimulation of Airflow in the Human Nasal Cavity," J. Biomech. Engr., Nov. 1995, vol. 117, 429–441.
Stradling et al., "New Approaches to Monitoring Sleep–Related Breathing Disorders," Sleep, Jun. 1996; vol. 19(9), S77–S84.
Tatara et al., "An Apnea Monitor Using a Rapid–Response Hygrometer," J. Clin. Monit., 1997; vol. 13, 5–9.
Dalmasso et al., "Snoring: Analysis, Measurement, Clinical Implications and Applications," Eor Respir. J., Jan. 1996; vol. 9(1), 146–159.

*Primary Examiner*—Mary Beth Jones
(74) *Attorney, Agent, or Firm*—Michael W. Haas

(57) ABSTRACT

A patient monitoring apparatus for quantatively measuring a physiological characteristic of a patient. A first patient interface communicates with an airway of a patient such that substantially all gas inhaled and exhaled by the patient passes through the first patient interface. One or more vent elements associated with the first patient interface communicate the first patient interface with an ambient atmosphere so that a pressure differential is created between the pressure in the first patient interface and the pressure of the ambient atmosphere. A sensor communicates with the first patient interface and measures a fluid characteristic resulting from this pressure differential and outputs a first signal indicative of that characteristic. The output from the sensor is used alone, or in combination with the output from other sensors that detect other physiological characteristics, to provide a variety of information about the patient.

10 Claims, 18 Drawing Sheets

U.S. PATENT DOCUMENTS

| | | |
|---|---|---|
| 4,170,899 A | 10/1979 | Fujita et al. |
| 4,173,891 A | 11/1979 | Johnson |
| 4,178,919 A | 12/1979 | Hall |
| 4,259,967 A | 4/1981 | Vooren et al. |
| 4,285,245 A | 8/1981 | Kennedy |
| 4,506,553 A | 3/1985 | Bruce et al. |
| 4,523,481 A | 6/1985 | Steen |
| 4,548,076 A | 10/1985 | Haake et al. |
| 4,599,895 A | 7/1986 | Wiseman |
| 4,754,651 A | 7/1988 | Shortridge et al. |
| 4,796,651 A | 1/1989 | Ginn et al. |
| 4,829,449 A | 5/1989 | Polesnak |
| 4,905,709 A | 3/1990 | Bieganski et al. |
| 4,989,456 A | 2/1991 | Stupecky |
| 5,006,109 A | 4/1991 | Douglas et al. |
| 5,033,312 A | 7/1991 | Stupecky |
| 5,038,621 A | 8/1991 | Stupecky |
| 5,060,655 A | 10/1991 | Rudolph |
| 5,063,938 A | 11/1991 | Becket et al. |
| 5,107,860 A | 4/1992 | Malouvier et al. |
| 5,111,827 A | 5/1992 | Rantala |
| 5,137,026 A | 8/1992 | Waterson et al. |
| 5,170,798 A | 12/1992 | Riker |
| 5,357,972 A | 10/1994 | Norlien |
| 5,357,975 A | 10/1994 | Kraemer et al. |
| 5,367,910 A | 11/1994 | Woodward |
| 5,501,231 A | 3/1996 | Kaish |
| 5,535,739 A | 7/1996 | Rapoport et al. |
| 5,546,933 A | 8/1996 | Rapoport et al. |
| 5,564,432 A | 10/1996 | Thomson |
| 5,685,296 A | 11/1997 | Zdrojkowski et al. |
| 5,722,417 A | 3/1998 | Garbe |
| 5,743,270 A | 4/1998 | Gazzara et al. |
| 5,803,066 A | 9/1998 | Rapoport et al. |
| 6,142,952 A | 11/2000 | Behbehani et al |

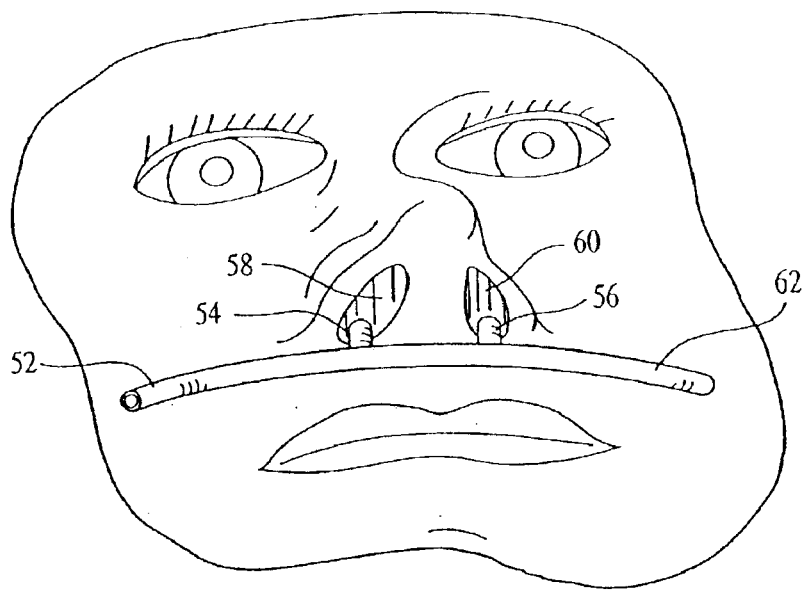
FIG. 3
(PRIOR ART)
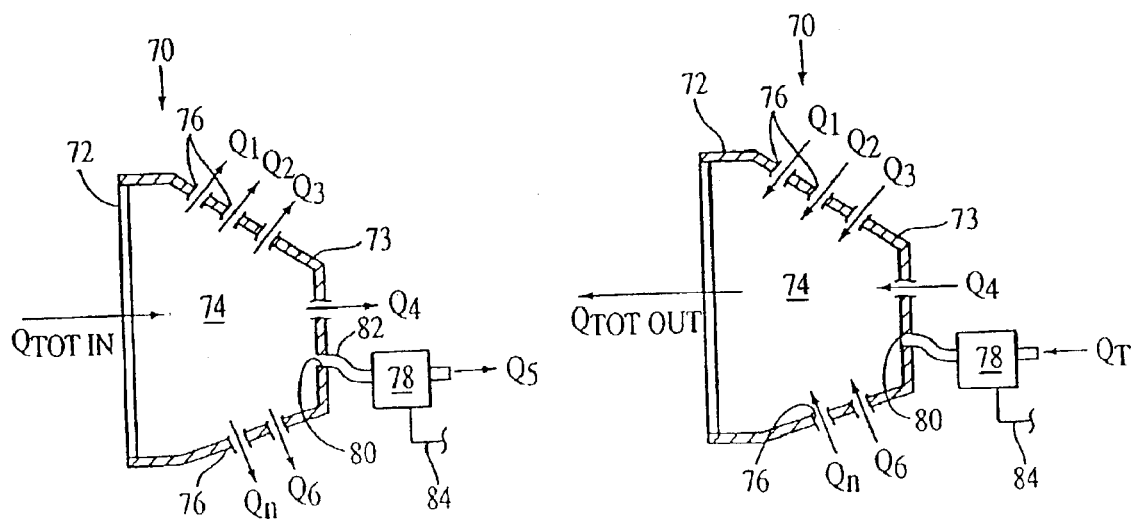
FIG. 4A
FIG. 4B

PATIENT MONITOR AND METHOD OF USING SAME

CROSS-REFERENCE TO RELATED APPLICATIONS

This is Continuation of U.S. patent application Ser. No. 09/961,618 filed Sep. 24, 2001, now U.S. Pat. No. 6,544, 192: which is a Continuation-in-Part (CIP) of U.S. patent application Ser. No. 09/438,081 filed Nov. 10, 1999, now U.S. Pat. No. 6,342,040; which is a Continuation of U.S. patent application Ser. No. 09/030,221 filed Feb. 25, 1998, now U.S. Pat. No. 6,017,315.

BACKGROUND OF THE INVENTION

1. Field of the Invention

The present invention pertains to a patient monitor for monitoring and/or quantitatively measuring a physiological characteristic of the patient, and, in particular, to an apparatus and method for monitoring and/or quantitatively measuring a physiological characteristic based, at least in part, on a pressure differential between a pressure within a user interface and an ambient atmospheric pressure outside the user interface.

2. Description of the Related Art

There are many situations in which it is necessary or desirable to measure a physiological characteristic of a patient, such as characteristics associated with respiration. Examples of characteristics associated with respiration include the patient's flow, inspiratory period, expiratory period, tidal volume, inspiratory volume, expiratory volume, minute ventilation, respiratory rate, ventilatory period, and inspiration to expiration (I to E) ratio. It is also important in many situations to identify still other characteristics associated with respiration, such as identifying the start, end and duration of a patient's inspiratory phase and expiratory phase, as well as detecting patient snoring. For example, when conducting a sleep study to diagnose sleep disorders or when conducting other pulmonary monitoring functions, it is common to measure the respiratory rate and/or the air flow to and from the patient. Distinguishing between inspiration and expiration is useful, for example, in triggering a pressure support device that provides breathing gas to a patient.

There are several known techniques for monitoring patient breathing for these purposes. A first conventional technique involves placing a thermistor or thermocouple in or near the patient's airway so that the patient's breath passes over the temperature sensing device. Breathing gas entering the patient has a temperature that is generally lower than the exhaled gas. The thermistor senses this temperature difference and outputs a signal that can be used to distinguish between inspiration and expiration. A primary disadvantage of the thermistor or thermocouple air flow sensing technique is that these devices cannot quantitatively measure the flow and/or volume of breathing gas delivered to and/or exhaled from the patient, because the signal from the sensor is a measure of air temperature, not air flow or pressure. Typically, a thermistor air flow sensor is only used to differentiate between inspiration and expiration. Sensors that detect humidity have similar uses and similar disadvantages.

A second conventional technique for measuring the airflow to and from a patient is illustrated in FIG. 1 and involves placing a pneumotach sensor 30 in a breathing circuit 31 between a supply of breathing gas, such as a ventilator or pressure support device, and the patient's airway. In a conventional pneumotach, the entire flow of breathing gas $Q_{IN}$ is provided to a patient 32 from a pressure source 34. Conversely, all of the gas expelled from patient 32, passes through pneumotach 30 so that during operation, there is a two-way flow of gas through pneumotach 30.

In its simplest form shown in FIG. 1, pneumotach 30 includes a flow element 36 having an orifice 38 of a known size defined therein. Flow element 36 provides a known resistance R to flow through the pneumotach so that a pressure differential $\Delta P$ exists across of flow element 36. More specifically, flow element 36 causes a first pressure P1 on a first side of the flow element to be different than a second pressure P2 on a second side of the flow element opposite the first side. Whether P1 is greater than P2 or vice versa depends on the direction of flow through the pneumotach.

In a first type of conventional pneumotach, a major portion $Q_1$ of the total flow $Q_{IN}$ of gas delivered to pneumotach 30 passes through orifice 38. The pressure differential $\Delta P$ created by flow element 36 causes a lesser portion $Q_2$ of the gas delivered to the pneumotach to be diverted through a bypass channel 40, which is connected to breathing circuit 31 across flow element 36. An airflow sensor 42 in bypass channel 40 measures the flow of gas therethrough. Because the area of orifice 38 and the area of bypass channel 40 are known and fixed relative to one another, the amount of gas $Q_2$ flowing through bypass channel 40 is a known fraction of the total gas flow $Q_{IN}$ delivered to pneumotach 30. Airflow sensor 42 quantitatively measures the amount of gas $Q_2$ passing through bypass channel 40. Once this quantity is known, the total flow $Q_{IN}$ of gas passing through pneumotach 30 can be determined.

In a second type of conventional pneumotach, a pressure sensor, rather than an airflow sensor, is provided in bypass channel 40. Gas does not pass through the pressure sensor. Instead, each side of a diaphragm in the pressure sensor communicates with respective pressures P1 and P2 on either side of flow element 36. The pressure sensor measures pressure differential $\Delta P$ across flow element 36. For example, for flow in the direction illustrated in FIG. 1, pressure differential $\Delta P$ across flow element 36 is P1−P2. Once pressure differential $\Delta P$ is known, the flow rate $Q_{IN}$ of gas passing through pneumotach 30 can be determined using the equation, $\Delta P=RQ^2$, where R is the known resistance of flow element 36.

Another conventional pneumotach 44 is shown in FIG. 2. Pneumotach 44 improves upon pneumotach 30 in FIG. 1 by providing a first linear flow element 46 in place of flow element 36. First linear flow element 46 functions in the same manner as flow element 36 by creating a pressure differential in breathing circuit 31. However, flow element 46 has a plurality of honey-comb like channels that extend in the direction of gas flow to linearize the flow of gas through the pneumotach. The previous flow element 36 in FIG. 1 can create downstream turbulence that hinders the flow of gas through the bypass channel or causes fluctuations in the downstream pressure, thereby degrading the airflow or pressure differential signal output by sensor 42. Flow element 46 solves this problem by providing a plurality of honeycomb-like channels having longitudinal axis parallel to the axis of the breathing circuit. The honeycomb channels ensure that the flow across the downstream port of the bypass channel is linear, i.e., non-turbulent.

To ensure that the flow of gas across the port in bypass channel 40 upstream of flow element 46 is also linear, i.e., non-turbulent, other linear flow elements 48 and 50 are provided in the breathing circuit. Flow elements 48 and 50 have the same honeycomb configuration as flow element 46. Because gas can flow in both directions through pneumotach 44, flow elements 48 and 50 are respectively located on each side of flow element 46 so that each entry port for bypass channel 40 is downstream of one of these additional flow elements regardless of the direction of flow through the pneumotach.

Although a pneumotach improves upon a theremistor in that it quantatively measures the flow and/or volume of gas passing therethrough, it also has significant disadvantages. For example, a pneumotach is relatively complicated and therefore difficult and costly to manufacture. It is also difficult to clean and is relatively large. Because of its size, which is dictated by the need to measure the pressure differential or flow across the flow element in the breathing circuit, it creates a relatively large amount of dead space in the patient breathing circuit, which is not conducive to minimizing rebreathing of $CO_2$. Because of its complexity, a pneumotach may leak, and its operating capabilities can suffer as a result of heat and moisture buildup.

A third type of conventional airflow meter, illustrated in FIG. 3, is a nasal cannula airflow meter 52. Nasal cannula airflow meter 52 is similar to a nasal oxygen cannula in that it includes a pair of ports 54 and 56 that insert into nares 58 and 60 of the user. A hollow tubing 62 carries a fraction of the total amount of breathing gas to a sensor, such as an airflow or pressure sensor. If the total area of the user's nares relative to the total area of the ports 54 and 56 is known, the nasal cannula airflow meter can provide a quantitative measure of the patient airflow.

However, because the total area of each user's nares can vary from person to person, a commonly sized nasal cannula airflow meter cannot provide an accurate, quantitative measure of the airflow for all users. If two people have different sized nasal openings, the fraction of the exhaled air that is being delivered to the ports of the nasal cannula cannot be known for both users. For example, a first user may deliver 30% of the exhaled gas to the ports of the nasal cannula, while a second user may deliver only 10% of the exhaled to the same sized nasal cannula. This variation in the percentage of gas delivered to the same size cannula is due to the variation in the total cross-sectional area of the nares of both users. For the same size nasal cannula, a user with larger nares will deliver a smaller percentage of the total exhaled gas to the ports of the nasal cannula than a user with smaller nares. Thus, a conventional nasal cannula cannot accurately measure the airflow for a plurality of users having different sized nares.

In addition to detecting and measuring quantities associated with the rate of volume of air being delivered to a patient, there are also many instances where it is important to detect other characteristics associated with respiration, such as snoring. The onset of snoring and/or the intensity of snoring can be used, for example, as a trigger to initiate or control the level of a positive pressure therapy provided the patient. Also, the presence, intensity and/or duration of snoring can be used as a diagnostic tool in determining whether the patient suffers from a sleep and/or breathing disorder.

It is known to use a microphone or pressure sensor mounted on the exterior of the patient's neck to detect sounds or throat vibrations generated by the snore. In many situations, these sensors are mounted on the user as an individual unit and are not connected to other structures worn by the patient. This can result in incorrect or inefficient placement of such sensors. Also, conventional snore sensing devices are quite susceptible to noise. For example, microphones can pick up external sounds not produced by the patient, such as snoring of a person or animal near the patient, and/or sounds not resulting from snoring, such as coughing. Pressure sensors can be adversely effected by body movements, such as normal movements that take place during the night and/or throat vibrations resulting from coughing.

SUMMARY OF THE INVENTION

Accordingly, it is an object of the present invention to provide a patient monitoring device for monitoring and/or quantitatively measuring a physiological characteristic of the patient, and, in particular, a characteristic associated with respiration, that does not suffer from the disadvantages of convention airflow/volume meters and snore detectors. This object is achieved by providing a patient monitoring apparatus that includes a first patient interface adapted to be located at a first orifice of a patient such that substantially all gas passing through the first orifice passes through the first user interface. At least one vent element is provided in or near the first patient interface to communicate a portion of gas passing through the first patient interface with an ambient atmosphere. This creates a pressure differential between the pressure within the first patient interface and the ambient atmospheric pressure. A first sensor coupled to the first patient interface measures a fluid characteristic resulting from the pressure differential, and a processing unit determines a quantitative value for a physiological characteristic of the patient based on signal output by the first sensor.

It is yet another object of the present invention to provide a patient monitoring method for quantitatively measuring a physiological characteristic of the patient that does not suffer from the disadvantages of conventional patient monitoring methods. This object is achieved by providing a method that includes locating a first patient interface at a first orifice of a patient such that substantially all gas passing through the first orifice passes through the first user interface. The first patient interface includes at least one vent element that communicates a portion of gas passing through the first patient interface with an ambient atmosphere, thereby creating a first pressure differential between a pressure within the first patient interface and the ambient atmospheric pressure. Gas is then passed through the first patient interface to create the first pressure differential, and a first fluid characteristic resulting from the pressure differential, such as the rate of flow of gas through a sensor or the pressure in the interface, is measured. From this measurement, the present method determines a first quantitative value for a physiological characteristic of the patient based.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

BRIEF DESCRIPTION OF THE DRAWINGS

FIG. 3 is a schematic diagram of a conventional nasal cannula airflow meter;

FIGS. 4A and 4B schematically illustrate a first embodiment of first portion of an interface meter according to the principles of the present invention;

DETAILED DESCRIPTION OF THE PRESENTLY PREFERRED EMBODIMENTS OF THE INVENTION

Figure 1:
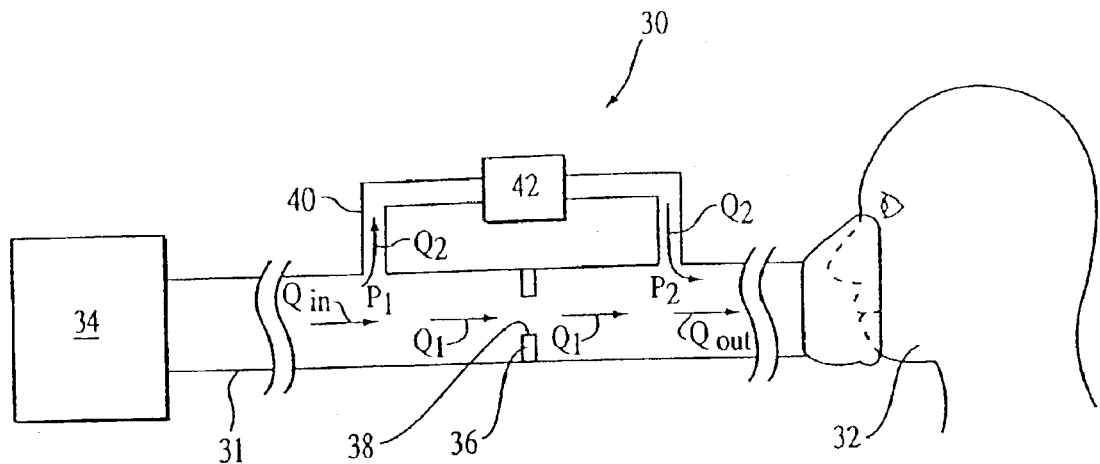
FIGS. 1–2 are schematic diagrams of conventional pneumotach airflow meters.
Figure 2:
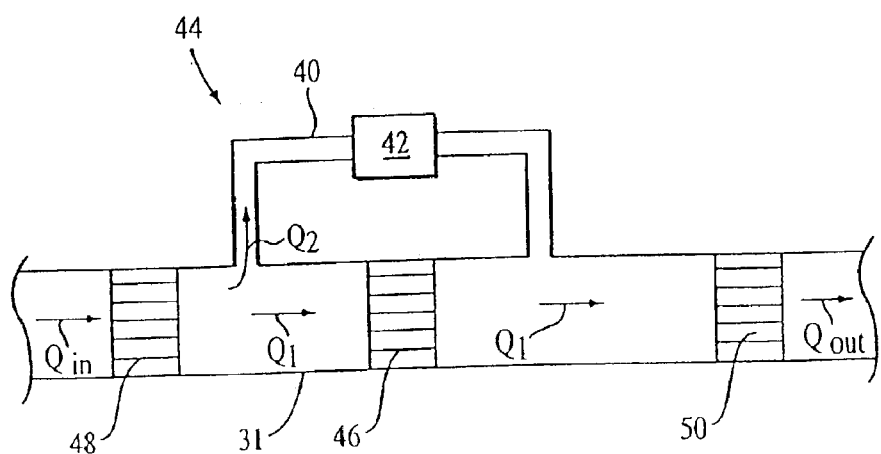

FIGS. 4A and 4B schematically illustrate a first embodiment of an interface meter 70 according to the principles of the present invention. Meter 70 includes a user interface 72, which in this embodiment is a mask worn over the nose and/or mouth of the patient (not shown). It should be noted that the terms "user" and "patient" are used synonymously through this document. A wall 73 of user interface 72 defines an interior portion 74 that receives the user's nose and/or mouth when worn by the patient. As the user breathes into the user interface, gas is transferred between the user and interior portion 74 of user interface 72. A plurality of holes 76 are provided in wall 73 of user interface 72 to exhaust exhaled gas from interior portion 74 to the ambient atmosphere outside user interface 72. See FIG. 4A. Conversely, gas inhaled by the user enters interior portion 74 of user interface 72 through holes 76 before being inhaled by the user. See FIG. 4B.

A sensor 78 is coupled to a hole 80 in the user interface to measure a fluid characteristic, such as a flow rate or a pressure differential, associated with the transfer of gas between interior portion 74 of user interface 72 and ambient atmosphere. In the embodiment illustrated in FIGS. 4A and 4B, sensor 78 is coupled to user interface 72 such that a portion of the gas entering or exiting interior portion 74 of user interface 72 passes through the sensor. The size and shape of sensor 78, hole 80 and a tubing 82 connecting sensor 78 to hole 80 are selected so as to minimize the resistance to flow between interior portion 74 and the area outside the mask imposed by sensor 78, hole 80 and tubing 82. In the illustrated embodiment, sensor 78 is an air flow meter that measures the rate of flow of gas passing through the meter.

Holes 76 provided in user interface 72 function in much the same manner as the flow element in a conventional pneumotach. Namely, holes 76 create a slight resistance to the flow of gas into or out of interior portion 74 of user interface 72 so that during inhalation and exhalation, a pressure differential is created between interior portion 74 of user interface 72 and the ambient pressure outside the mask. This pressure differential causes gas to flow through the circuit defined by tubing 82 and sensor 78 so that the rate of flow of gas through sensor 78 can be qualitatively measured by sensor 78.

For an incompressible fluid or gas, the flow of a fluid into an area must equal the flow of the fluid out of that area ($Q_{IN}=Q_{OUT}$). It should be noted that the terms "fluid" and "gas" are used interchangeably throughout this document. Applying this principle to interface 72, establishes that the flow of fluid into interior portion 74 from the user during exhalation $Q_{TOT\ IN}$ must equal the flow of fluid $Q_1, Q_2, \ldots Qn$ from the mask out holes 76, assuming that there are no unaccounted for leaks in the mask or at the user/mask interface. See FIG. 4A. Similarly, the flow to the user during inhalation $Q_{TOT\ OUT}$ must equal the flow into the mask through holes $Q_1, Q_2, \ldots Qn$, again, assuming that there are no unintentional leaks in the mask or at the user/mask interface. See FIG. 4B. Thus, $Q_{TOT}=Q_1+Q_2+\ldots Qn$.

While the illustrated embodiment describes the mask interface as having a plurality of holes defined directly in the wall of the interface, it is to be understood that the present invention is not limited to this particular configuration for communicating the interior portion of the interface to the ambient atmosphere. On the contrary, the present invention contemplates that any venting structures that communicates the interior portion of the interface to the ambient atmosphere, while creating a sufficient pressure differential can be used.

For example, venting can be achieved in a mask that has no exhaust holes by attaching an adapter tube to the inlet/outlet port in the mask. Holes can be provided in the adapter tube that communicate the interior portion of the adapter tube, and hence the interior portion of the mask, to ambient atmosphere. The combined mask and adapter is equivalent to user interface 72 illustrated in FIGS. 4A and 4B. It can also be appreciated that the venting structures need not be provided directly in the mask. Also, the venting mechanism, such as holes 16, can have any shape, pattern, or number of holes so long as they function for their intended purpose—to communicate the interior of the user interface to ambient atmosphere while creating a sufficient pressure differential to produce a fluid characteristic that can be measured by sensor 78. Also, the venting mechanism need not be defined by fixed diameter holes. On the contrary, the diameter or degree of opening of the venting structure can vary.

In the illustrated embodiment of the present invention, the area of hole 80 is fixed relative to the total area of the remaining holes 76 in user interface 72, so that the flow of gas $Q_5$ out of the mask through sensor 78 is a known fraction of the total flow of gas out of interior portion 74 of user interface 72 during expiration. Conversely, the flow of gas $Q_5$ into the mask through sensor 78 is a known fraction of the total flow of gas into interior portion 74 during inspiration. Sensor 78 measures the flow of gas $Q_5$ passing therethrough in either direction and outputs a signal 84 indicative of that flow and of the direction of the flow through the sensor. The rate of flow through the sensor is a characteristic of the gas passing through the mask interface and, as noted above, results from the pressure differential created by the flow element, which in this embodiment is defined by providing holes directly in the mask.

Because the portion of gas passing through sensor 78 is a known fraction of the total amount of gas passing through holes 76 and 80, the total flow of gas to and from the interior portion of user interface 72 can be determined from the measured flow through meter 78. Ideally, the measured flow through sensor 78 is linearly related to the total flow $Q_{TOT}$ into or out of interior portion 74 of user interface 72, so that once the flow through sensor 78 is known, the total flow into or out of the mask can be readily determined by applying a multiplying factor to signal 84 output from sensor 78. This can be accomplished, for example, by amplifying signal 84 by a predetermined amount.

It has been determined, however, that the flow measured by sensor 78 is typically not linearly related to the total flow through the user interface. This is so because the relationship between the total flow $Q_{TOT}$ through interior portion 74 of user interface 72 and the measured flow through sensor 78 is dependent upon a number of factors, such as the number and size of holes 76, the shape of interface 72, the distance of the sensor sampling port from the pressure source, the resistance to flow through the sensor and associated components, and the location of hole 80 in the mask to which the sensor is attached. Thus, additional processing typically must be performed on signal 84 before that signal accurately indicates the actual total flow through the user interface.

Regardless of whether the relationship between the flow through the sensor and the total flow through the mask is linear or non-linear, as long as the structure of the interface meter does not change, the determination of the total flow $Q_{TOT}$ into interior portion 74 of user interface 72 using the measured flow through sensor 78 will be substantially the same for all users regardless of the physical characteristics of the patient wearing the interface meter. Thus, once sensor 78 is calibrated for a particular interface 72 with fixed structural features, i.e., once the relationship between the output of sensor 78 to the total flow through the mask interface is established, the same interface meter 70 can be used on a wide variety of patients to measure characteristics associated with respiration quantitatively, such as the flow and/or volume of gas provided to the patient.

In a preferred embodiment of the present invention, sensor 78 is a mass airflow sensor, such as the AWM2100V sensor manufactured by Honeywell Inc., which outputs a range of analog voltages corresponding to a predetermined range of airflow rates through the sensor. The output from the AWM2100V is a positive and negative differential signal that corresponds to the rate and direction of flow through the sensor. The AWM2100V sensor is particularly well suited for use in measuring the amount of gas passing through a portion of user interface 72 because the AWM2100V is capable of accurately measuring a very small flow. For example, it has been determined that the pressure drop needed to generate flow across the AWM2100V at full scale is only 0.5 cm $H_2O$. Because the flow of breathing gas through sensor 78 can be quite small, the pressure drop across user interface 72 needed to create a flow through the AWM2100V is also quite small. As a result, user interface 72 can have an extremely low resistance so that gas flows relatively easily into and out of interior portion 74. Decreasing the flow resistance, which is accomplished by reducing the pressure drop across the user interface, i.e., across the flow element defined by the mask and the holes in the mask, is achieved, for example, by providing more holes in the mask and/or increasing the size of the holes so that breathing gas flows more freely between interior portion 74 and the area outside user interface 72.

One advantage achieved by making the mask resistance as low as possible is to provide a good (leak free) mask seal with the patient. The lower the mask resistance, the more likely there will be no leaks at the mask/patient interface. Unintentional leaks in the mask or in the mask/patient interface can be taken into consideration in determining the total flow to and from the patient based on the measured flow through sensor 78. For example, the leak estimation algorithms taught by U.S. Pat. Nos. 5,148,802; 5,239,995; 5,313,937; 5,433,193; and 5,632,269, the contents of which are incorporated herein by reference, can be used to determine unintentional leaks in the mask or mask/patient interface. If these unintentional leaks are minimized to an insubstantial amount, the use of leak estimation and correction techniques can be avoided.

It has been determined that a good seal is achieved as long as the pressure within interior portion 74 of user interface 72 is between −2 cm $H_2O$ to 2 cm $H_2O$. The relatively low flow resistance through the AWM2100V allows the pressure within the mask to be within this range. Thus, the assumption that there are no mask leaks other than through holes 76 and 80 is valid. For example, it has been determined that the pressure in user interface 72, even with the pressure drop caused by tubing 82 and a bacteria filter (not shown) placed between user interface 72 and sensor 78, is 1 cm $H_2O$ at a flow rate of 100 liters per minute (1 pm).

In any event, even if the pressure drop needed to generate flow across the sensor exceeds 2 cm $H_2O$, unintentional leaks at the mask/patient interface can be eliminated by increasing the sealing force applied on the mask to hold the mask on the patient and/or by providing an improved seal between the mask and user, such as an adhesive seal or a larger sealing area.

The present invention also contemplates that sensors other than an airflow sensor can be use as sensor 78. For example, sensor 78 can be a pressure sensor. An example of a suitable pressure sensor in a differential pressure sensor that directly measures the differential between interior portion 74 of user interface 72 and a pressure of the ambient atmosphere outside the user interface. This pressure differential, like the flow of gas through the sensor in the previous embodiment, is due to the restriction in flow between ambient atmosphere and the interior of the mask created by the flow element, which in this embodiment is defined by the holes provided in user interface 72. Another suitable sensor is an absolute pressure sensor that measures the pressure of interior portion 74 relative to a fixed reference pressure. Any sensor, such as an airflow, pressure or quantitative temperature sensor, that is capable of measuring a fluid characteristic created by the pressure differential caused by the flow element and that is capable of outputting a signal indicative of that characteristic can be used as sensor 78.

If sensor 78 is a pressure sensor, gas does not pass through the sensor. Instead, for a differential pressure sensor, one side of a diaphragm in sensor 78 communicates with interior portion 74 of user interface 72 and the other side of the diaphragm communicates with ambient atmosphere. The pressure sensor measures the pressure differential $\Delta P$ between a first pressure within the interior portion of the user interface and the ambient atmospheric pressure outside the user interface. Once this pressure differential is known, the actual flow rate $Q_{IN}$ of gas passing through the mask interface can be determined, for example, using a look-up table based on the known relationship between pressure and flow, i.e., $\Delta P = RQ^2$. A similar approach is used of the pressure sensor is an absolute pressure sensor.

Regardless of whether sensor 78 is an airflow sensor, a pressure sensor, or any other type of sensor, the signal output by the sensor is typically an analog signal. If sensor 78 is an airflow sensor, signal 84 corresponds to the rate of flow of gas through the sensor and indicates the relative direction of flow. If sensor 78 is a differential pressure sensor, signal 84 corresponds to a pressure differential across the flow element and also indicates a relative direction of flow based on whether the pressure within the interface is greater or less than ambient pressure. It can be appreciated that signal 84 corresponds to a characteristic associated with respiration because signal 84 can be used to quantitatively determine a characteristic associated with respiration, such as patient flow or volume. Even in its raw, uncalibrated form, signal 84 can be used to differentiate between inspiration and expiration and/or to detect snore, and thus, corresponds to the respiratory characteristic of inspiration, expiration and/or snore. The value of analog signal 84 represents a valve of one of these characteristics of respiration. Examples, of characteristics associated with respiration that can be determined using signal 84 are discussed in greater detail below.

Figure 5:
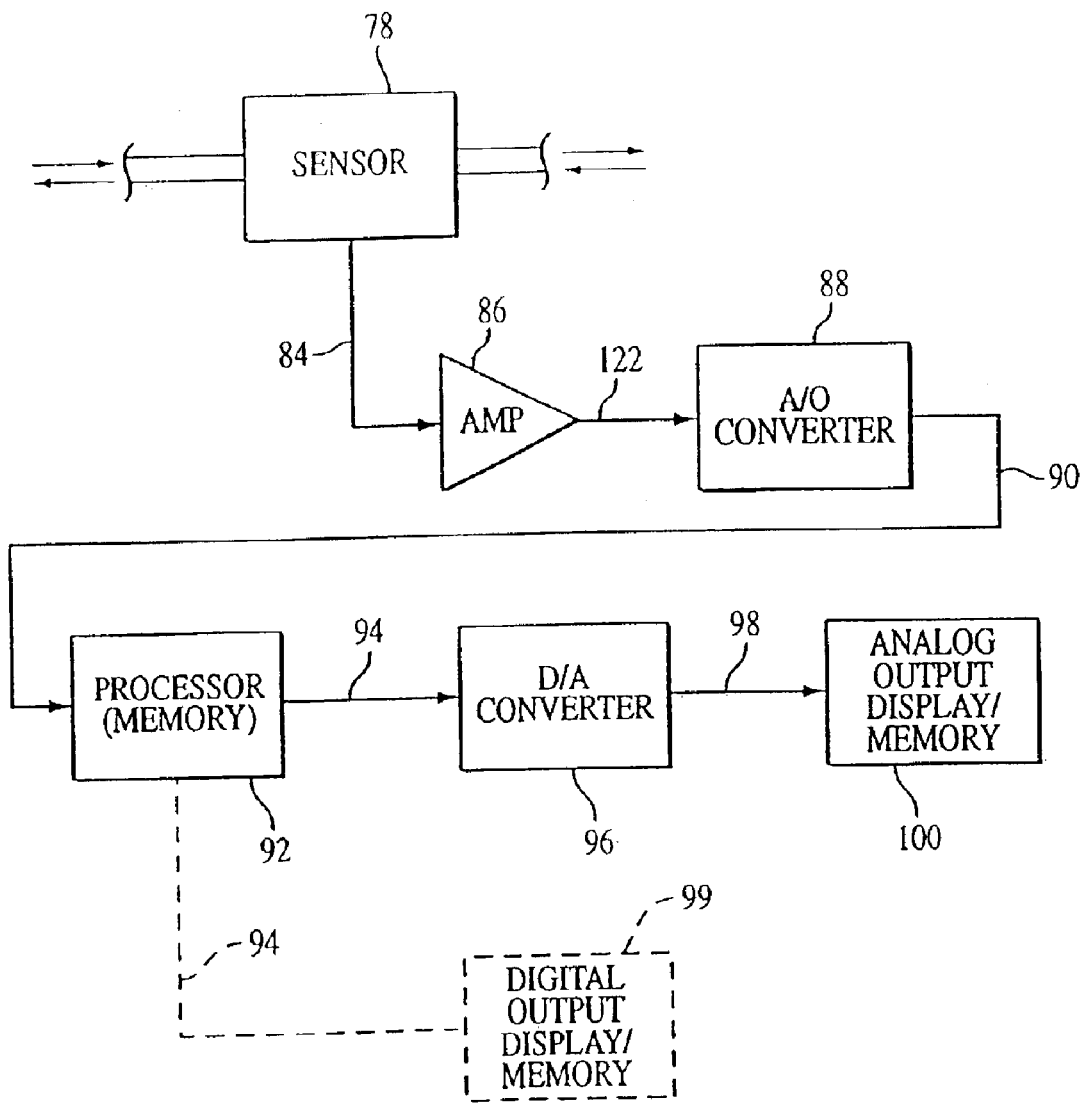
FIG. 5 is a schematic diagram a second portion of the interface meter illustrated in FIG. 4.

As shown in FIG. 5, signal 84 from sensor 78 is provided to an amplifier 86 and the output of amplifier 86 is provided to an analog-to-digital (A/D) converter 88. The digital output 90 of A/D converter 88 is provided to a processor 92 that corrects for the non-linearity in the output of sensor 78 so that the signal 94 output from processor 92 is a digital signal indicative of a quantitative value for a characteristic associated with respiration.

For example, in one embodiment of the present invention discussed above, signal 84 from sensor 78 is a signal indicative of the rate of flow of gas through the sensor. However, as discussed above, this signal is typically not linearly related to the total rate of flow of gas $Q_{TOT}$ to or from the interior portion 74 of the user interface. To correct for this non-linearity, signal 84 is provided to processor 92. Processor 92 determines the quantitative (actual) value for the total flow of gas $Q_{TOT}$ entering or exiting the interior portion 74 of user interface 72 based on signal 84. The details as to how this is accomplished are discussed below. It is to be understood, that based on signal 84, processor 92 can determine characteristics associated with respiration other than flow rate. For example, by integrating the corrected flow signal, processor 92 can output a signal representing the total volume of gas $V_{TOT}$ exiting or entering the interior portion of the user interface.

In the illustrated embodiment, a digital-to-analog converter 96 converts signal 94 from processor 92 into an analog signal 98 and provides analog signal 98 to an output and/or storage device 100. In a preferred embodiment of the present invention, output device 100 is a monitor or an LED display, that converts signal 98 into a human perceivable output indicative of the characteristic associated with respiration, such as rate or volume of flow to and from the user. It is also preferable to store signal 98 in a memory for use in evaluating the respiratory conditions of the patient. Alternatively or in addition to the above embodiment, output 94 from processor 92 can be provided in its digital format to a digital output device 99, such as a digital display, memory, terminal, and/or communication system.

Figure 6:
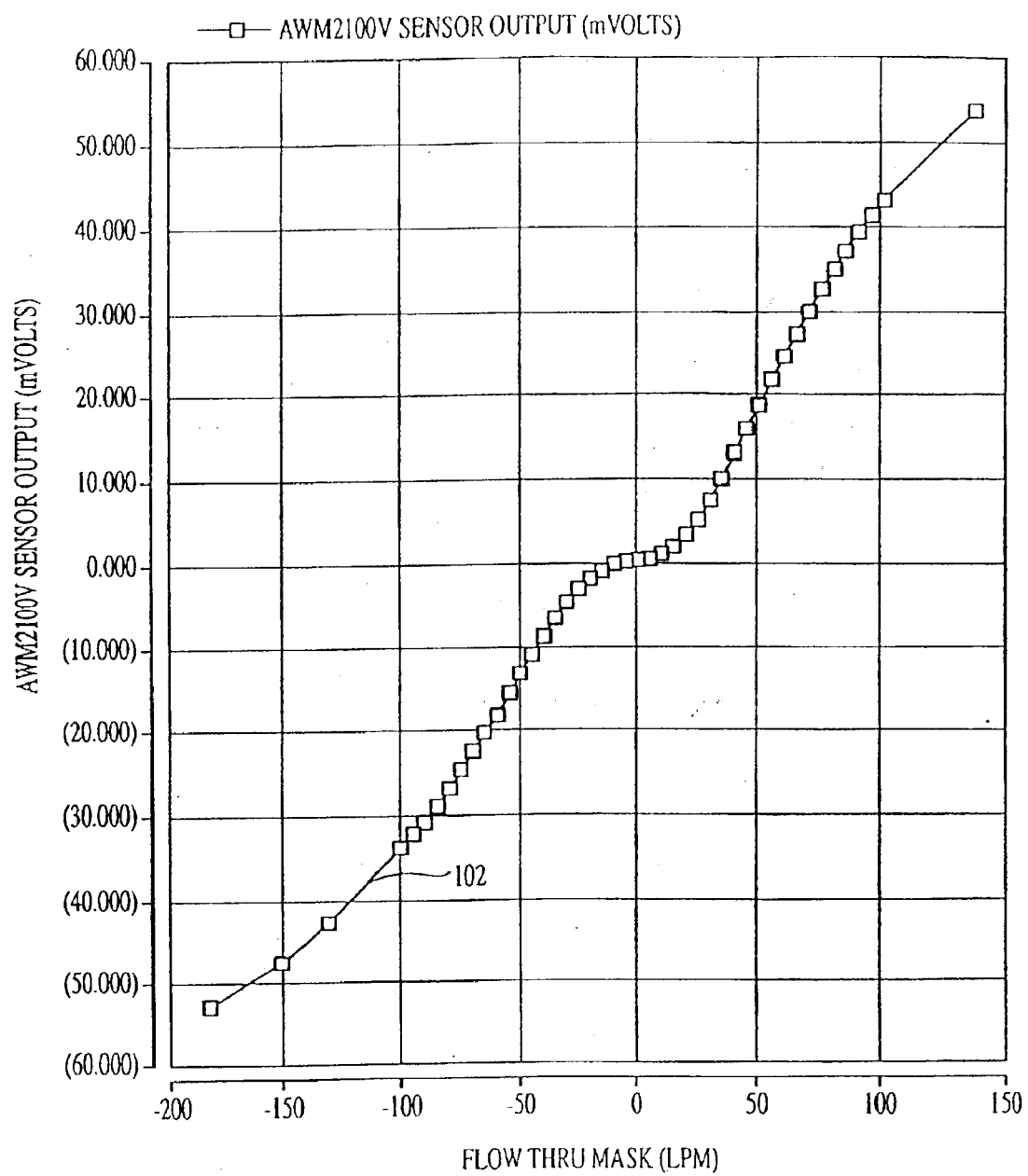
FIGS. 6, 7 and 8 are charts illustrating the relationship between the output from a sensor coupled to an interface device and the actual flow through the interface.

As noted above, because the output from sensor 78 is typically not linearly related to the rate of flow through the mask interface over the entire range of airflows to and from the patient, processor 92 must correct for the non-linearity in the output of sensor 78. In a preferred embodiment of the present invention, processor 92 calculates the total flow $Q_{TOT}$ entering or exiting interface 72 based on the output from sensor 78 using a lookup table, which is determined from a preestablished relationship between the output from sensor 78 and the flow through the interface. FIG. 6 is a graphical representation of this relationship. It should be understood that the graph in FIG. 6 is determined for a specific mask interface. The relationships established by the curve in FIG. 6 do not apply to all interfaces. Thus, for each different type of interface to which the processor is to be used, the relationship between the output of the sensor and the actual, quantitative value for the respiratory characteristic of interest must be determined beforehand so that this relationship can then be used to determine the quantitative value for the desired respiratory characteristic.

Curve 102 in FIG. 6 illustrates the relationship between the signal output by sensor 78 for a first type of mask interface and the flow through that interface. The vertical axis of the graph in FIG. 6 corresponds to the output of sensor 78, which is typically in a range of −60 mV to +60 mV for the AWM2100V sensor. The horizontal axis represents the total flow $Q_{TOT}$ into or out of the interface. The portion of curve 102 to the right of the zero flow mark on the horizontal axis represents flow in a first direction through the sensor, for example expiration, and the portion of curve 102 to the left of the zero flow point represents flow in a second direction, opposite the first direction, for example inspiration.

It can be appreciated from FIG. 6 that for the particular sensor and type of interface used to generate curve 102, the output from sensor 78 is not linearly related to the rate of flow through the mask interface. This is particularly true near the zero flow rate. However, by knowing the relationship between the output of sensor 78 and the total flow, the actual, quantitative flow through the mask can be readily determined.

It can be further appreciated that curve 102 will have different shapes depending on the type of sensor and interface being used. However, once the relationship between the sensor output and the flow through the interface is determined, this relationship remains valid independent of the physical characteristics of the patient using the interface meter. Thus, unlike nasal cannulas, the same interface meter can be used to quantitatively determine a characteristic associated with respiration, such as the flow rate, for a wide variety of users.

Figure 7:
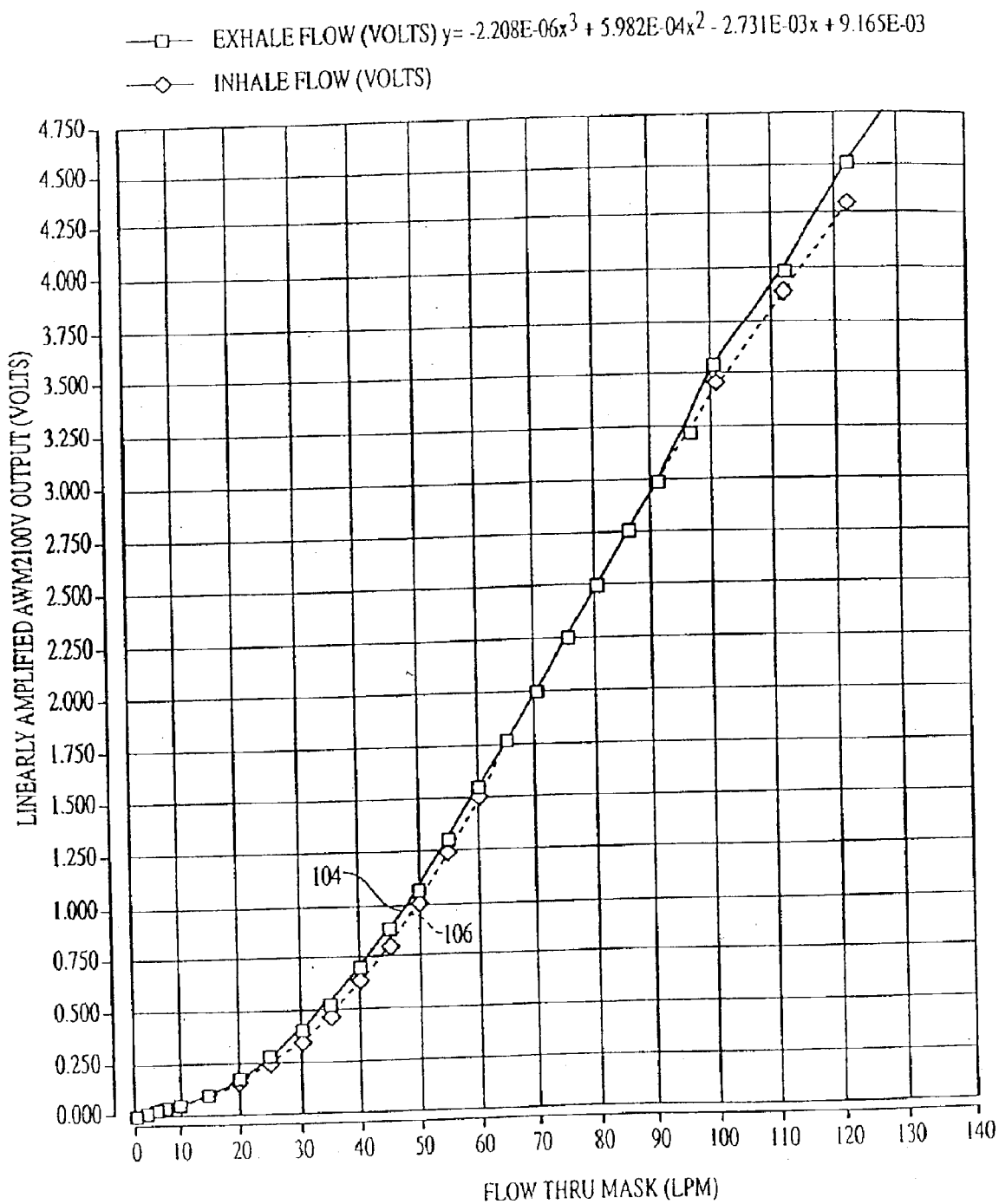

FIG. 7 is similar to FIG. 6 in that it is a graph illustrating the relationship between the signal output by sensor 78 for a particular type of mask interface and the flow through that interface. However, the vertical axis in FIG. 7 denotes a linearly amplified output of sensor 78, which corresponds to signal 122 in FIG. 5. The signal output from sensor 78 illustrated in FIG. 7 has been amplified so that the voltage range of the signal is between −5V and +5V. FIG. 7 includes a first curve 104, illustrated by a solid line, that represents the voltage-total flow relationship for flow through sensor 78 in a first direction (typically during exhalation) and a second curve 106, illustrated by a dotted line, that represents the voltage-total flow relationship for flow through sensor 78 in a second direction (typically during inhalation) opposite the first direction. In the illustrated embodiment, the output from sensor 78 is positive during expiration and negative during inspiration. It is to be understood, however, that this relationship could be reversed.

In FIG. 7, curves 104 and 106 representing the flow during expiration and inspiration, respectively, are superimposed on one another to demonstrate that the voltage-flow characteristics are substantially the same regardless of the direction of flow through sensor 78. Thus, the same relationship between the sensor output and the flow through the interface can be used regardless of the direction of flow through the interface, i.e., during inspiration and expiration, thereby simplifying the determination of the flow through the interface based on the measured output of sensor 78. It is possible, however, to use separate relationships to determine a quantitative value for a characteristic associated with inspiration and a characteristic associated with expiration.

In a preferred embodiment of the present invention, the known relationship between the output of sensor 78 and the flow through the mask interface, as illustrated by the curves in FIGS. 6 and 7 for example, is used to generate a lookup table. This table is used to determine the actual flow through the mask interface from the output of sensor 78. However, the present invention contemplates that techniques other than a look-up can be used to determine a quantitative measure of a characteristic associated with respiration from the raw signal output from sensor 78. For example, once the voltage-total flow relationship for the interface meter is established, the flow can be calculated from an equation defining this relationship. For example, curves 104 and 106 in FIG. 7 can be generally defined by the following third order polynomial equation:

$$y = -2.208 \times 10^{-6} x^3 + 5.982 \times 10^{-4} x^2 - 2.731 \times 10^{-3} x + 9.165 \times 10^{-3},$$

where y is the linearly amplified output of sensor 78 and x is the flow into or out of the mask interface. Once y is determined by sensor 78, processor 92 can solve for x to determine the total flow into or out of the interface. As noted above, separate equations or lookup tables can used to determine the flow through the mask during expiration and expiration, thereby improving the accuracy of the output of the interface meter if the relationship between the output of sensor 78 and flow through the interface is not the same for flow in both directions through the sensor.

It should be understood that the above equation and the graph illustrated in FIGS. 6 and 7 defining the relationship between the output of sensor 78 and the total flow into or out of the mask interface apply only to a particular type of interface having a predetermined structure. If, for example, more holes are added or the mask shape or size is altered, the relationship between the output of sensor 78 and the total flow into or out of the mask interface may change, requiring recalibration of processor 92 so that a different curve is used to determine the quantitative value for the desired respiratory characteristic based on the output of the sensor.

Figure 8:
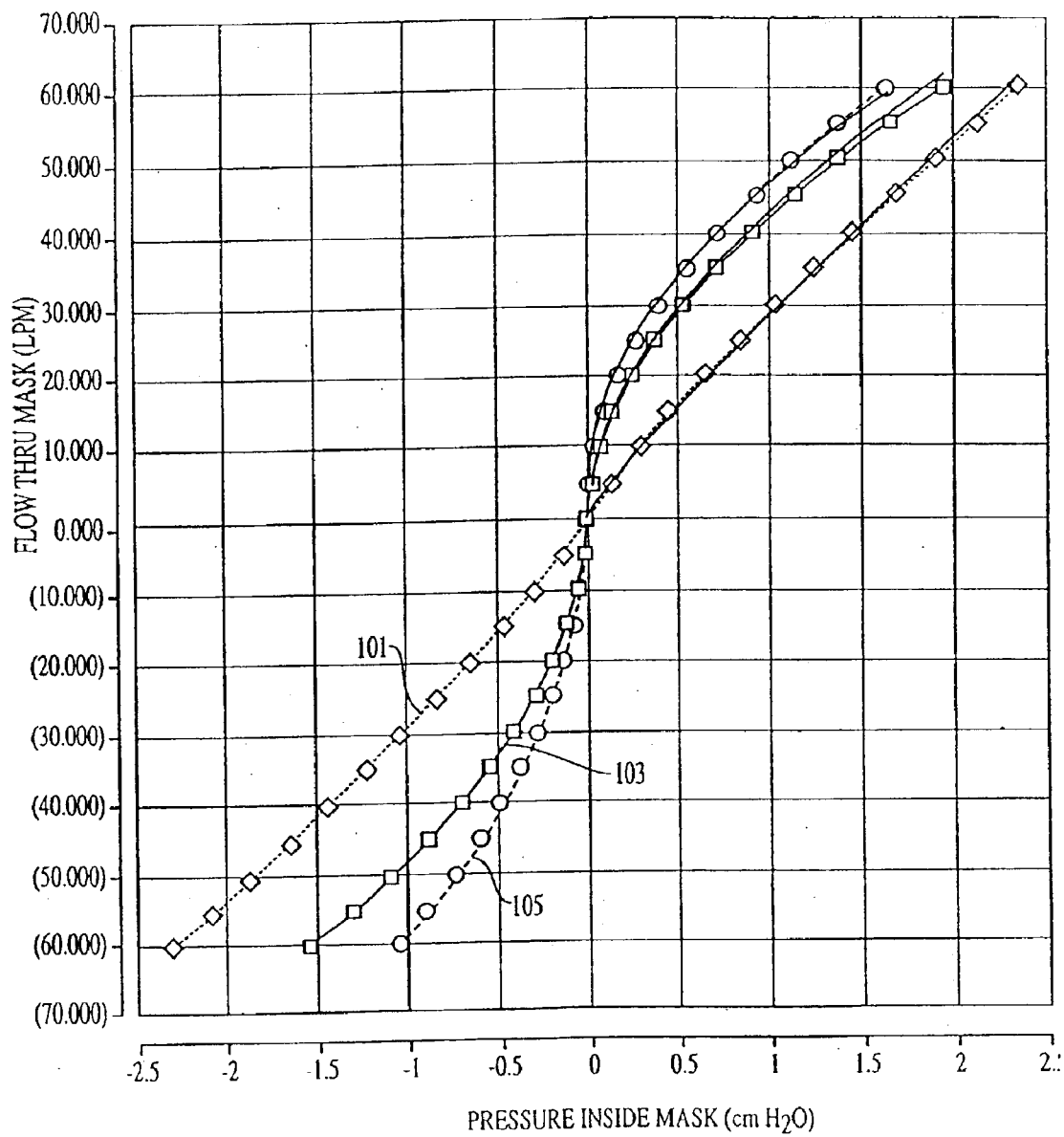

For example, FIG. 8 illustrates three curves 101, 103 and 105 defining the relationship between the pressure measured by sensor 78 and the flow through the interface for three masks having different structural characteristics. Curve 101 associated with a first mask is nearly a straight line, meaning that there is nearly a linear relationship between the pressure measured by sensor 78 and the total flow through the interface. FIG. 8 also demonstrates that if sensor 78 is a pressure monitor, the same techniques used to generate the total flow through the mask, i.e., using a look-up table or equation derived from the relationships illustrated in FIG. 8, can be used to determine the quantitative value for characteristic associated with respiration, such as flow through the interface.

So long as a batch of mask interfaces are manufactured with the same structural characteristics, the same calibration, i.e., voltage—flow curve, can be applied to all of the mask interfaces in that batch. By providing each processor with the same voltage-total flow relationship there is no need to calibrate each interface meter individually. In short, the interface meters of the present invention can be commonly calibrated so long as they share the same structural characteristics for the interface. The operating characteristics of the interface meter do not vary with the physical characteristics of the user, as is the case with conventional nasal cannula flow meters.

It is to be further understood that processor 92 can contain a number of different lookup tables and/or equations associated with a variety of different interface devices so that the same processor can be used in conjunction with a number of different types or configurations of patient interfaces, so long as the proper lookup table or voltage-total flow equation is used with the selected interface. In this embodiment, a selector is provided so that the user can select the type of interface being used with the interface meter.

In one embodiment of the present invention, the selector is a manually actuated mechanism operatively coupled to processor 92 that enables the user to select the appropriate correlation element associated with a particular user interface. Processor 92 then uses the correct lookup table or equation or other technique based on the output from the selector to determine the quantitative value for a patient's physiological characteristic based on the selected interface. For example, a memory portion in processor 92 can contain three lookup tables associated with three different mask sizes. The user selects the mask size being used and inputs this selection to processor 92 via a selector switch. Processor 92 then uses the correct lookup table for the selected mask size to determine the quantitative value for the flow through the mask interface based upon the output from sensor 78.

In a more sophisticated embodiment, the processor communicates with the interface to automatically determine the type of interface being used with that processor. For example, the processor can be operatively coupled to the interface via an electrical wire and can periodically interrogate the user interface via the wire. Each different user interface may provide a different response to the interrogation signal from the processor. Therefore, the response signal form the user interface tells the processor which lookup table or other calibration technique to use for that user interface.

As discussed above, a primary function of processor 92 in the present invention is to convert the signal from sensor 78 into a signal that accurately represents the flow of breathing gas into or out of the user interface. This is necessary because it is believed to be difficult to situate the various structural elements of the interface and sensor such that the signal output from sensor 78 is linearly related to the flow through the mask to which the sensor is attached. If, however, a suitable configuration can be established, the linearizing function performed by the processor will not be necessary. Instead, processor 92 will merely provide a multiplying function to calculate the total amount of breathing gas passing through the mask interface from the known fraction of breathing gas passing through sensor 78. Alternatively, processor 92 can be eliminated and the multiplying function can be performed using circuitry, for example, by adjusting the gain in amplifier 86 of FIG. 5.

Figure 9:
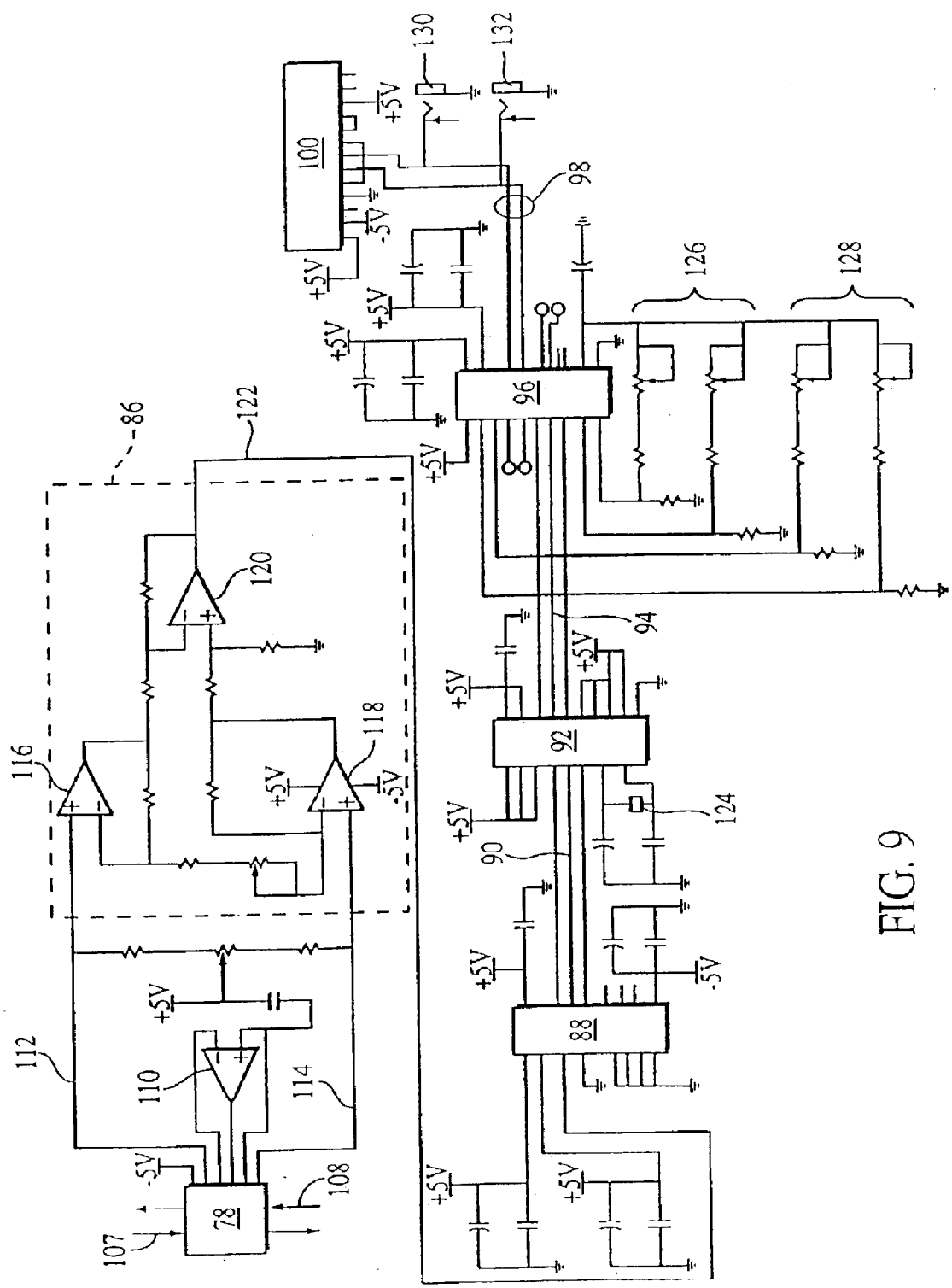
FIG. 9 is a more detailed circuit diagram of the interface meter illustrated in FIG. 5.

FIG. 9 is a more detailed diagram of the circuit schematically illustrated in FIG. 5. Gas passes through sensor 78 in a first direction, as indicated by arrow 107, during expiration and in a second direction opposite the first direction, as indicated by arrow 108, during inspiration. Amplifier 110 sets the control for a heater that is used in the Honeywell airflow sensor to measure the flow rate therethrough. Outputs 112 and 114 of sensor 78 are positive and negative differential signals representing the flow measured by sensor 78 and are provided to a pair of amplifiers 116 and 118, respectively. Outputs of amplifiers 116 and 118 are provided to a differential amplifier 120. Amplifiers 116, 118 and 120 define amplifier 86 in FIG. 5 and convert the dual outputs of sensor 78 into a single analog signal 122. In a preferred embodiment of the present invention, amplifiers 110, 116, 118 and 120 are provided on a same integrated circuit, such as the LMC660CN Quad OP-AMP manufactured by National Semiconductor.

Signal 122 from amplifier 86, which is referred to as a raw or uncalibrated signal because it typically does not linearly correspond to the respiratory characteristic of interest, is provided to A/D converter 88, such as an ADC10831 converter manufactured by National Semiconductor. Digital output 90 of A/D converter 88 is provided to processor 92. In the illustrated embodiment, processor 92 is the PIC16C84 manufactured by Microchip Inc. Processor 92 operates at a clock speed set by oscillator 124 to calculate the flow $Q_{TOT}$ entering or exiting interface 72, for example, based on the output from sensor 78 as discussed above. It is to be understood, that any combination of the circuit components illustrated in FIG. 9 can be provided on a single chip. For example, A/D converter 88, processor 92, and D/A converter can be fabricated on the same chip for ease of manufacturing the interface meter of the present invention.

In one embodiment of the present invention, processor 92 uses a lookup table or a voltage-total flow equation established for a particular type of interface 72 to determine the flow $Q_{TOT}$ entering or exiting the interface based on signal 90 from A/D converter 88. In the illustrated embodiment, output 94 of processor 92 is a signal indicative of the flow entering or exiting the interface and is provided to D/A converter 96 where it is converted into a pair of analog signals 98, which are positive and negative signals, respectively, depending on the direction of flow through sensor 78. In the illustrated embodiment D/A converter 96 is a DAC0854 converter manufactured by National Semiconductor. A first pair of variable resistors 126 set the positive gain for the analog output of D/A converter 96 and a second pair of variable resistors 128 set negative gain. Analog signals 98 are provided to a display 100, such as an LCD or LED display, where they are converted into an output that is capable of being perceived by humans.

In the illustrated embodiment, analog signals 98 are also provided to a pair of output terminals 130 and 132 so that signals 98, which represent the actual (quantitative) flow of breathing gas passing through the interface, can be provided to external components, such as a display, data storage device, alarm system, printer, additional processing elements, and/or data communication system, such as a modem. It is to be understood, however, that any of these components could be provided within the circuitry illustrated in FIG. 9 on the same card or circuit board.

Figure 10A:
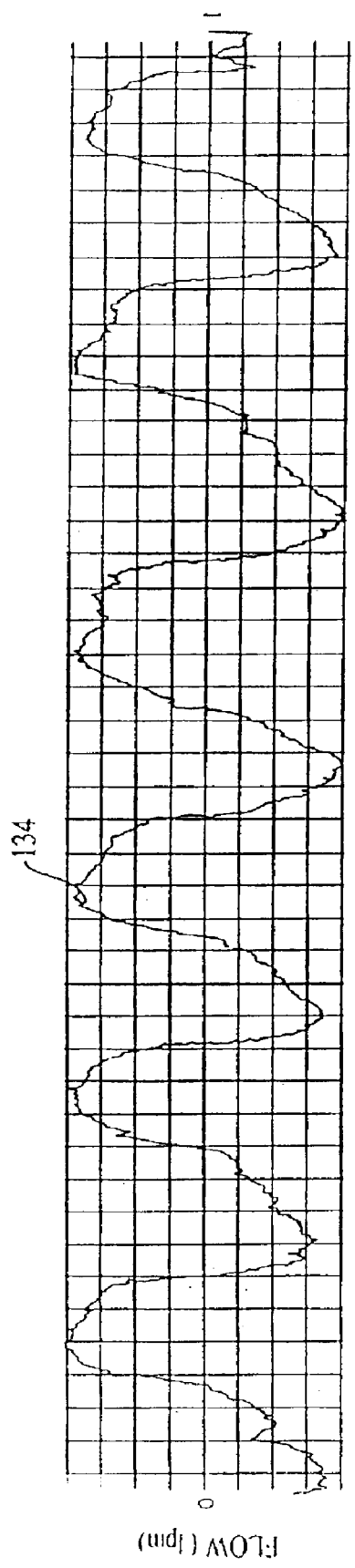
FIGS. 10A and 10B are waveforms illustrating the flow and volume of patient respiration measured using the interface meter according to the first embodiment of the present invention.
Figure 10B:
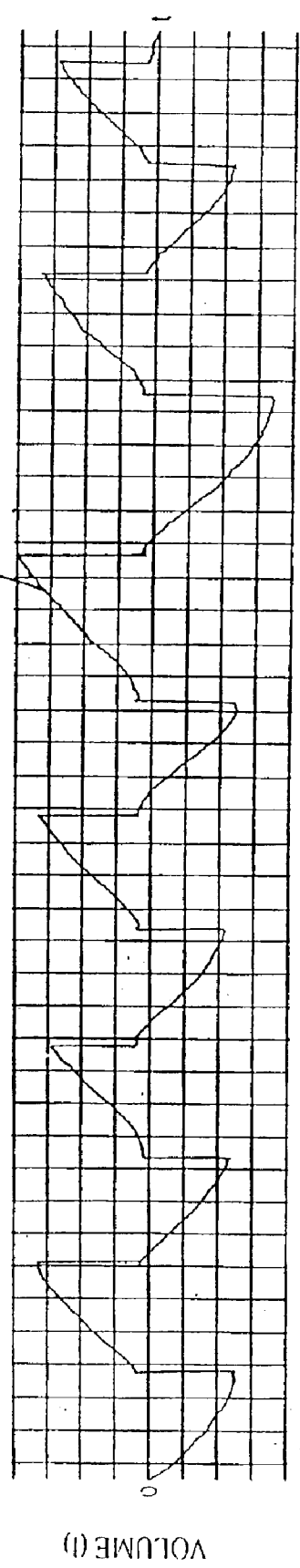

FIG. 10A illustrates a waveform 134 of the flow through sensor 78 during inspiration and expiration in liters per minute (1 pm) generated by a computer using signal 98 taken at terminals 130 and 132 in FIG. 9. FIG. 10A is one example of how the signal produced by processor 92 could be output in human perceivable format. FIG. 10B illustrates a waveform 136 of the tidal volume for the same flow rate of breathing gas passing through sensor 78 in liters, which is also generated by a computer using signal 98 taken at terminals 130 and 132. Waveform 136 in FIG. 10B can be generated, for example, by integrating the flow signal 134 illustrated in FIG. 10A. The smoothness of waveforms 134 and 136 illustrated in FIGS. 10A and 10B can be improved by increasing the processing speed of processor 92. This could be accomplished, for example, by increasing the oscillating frequency of oscillator 124 in FIG. 9.

Figure 11A:
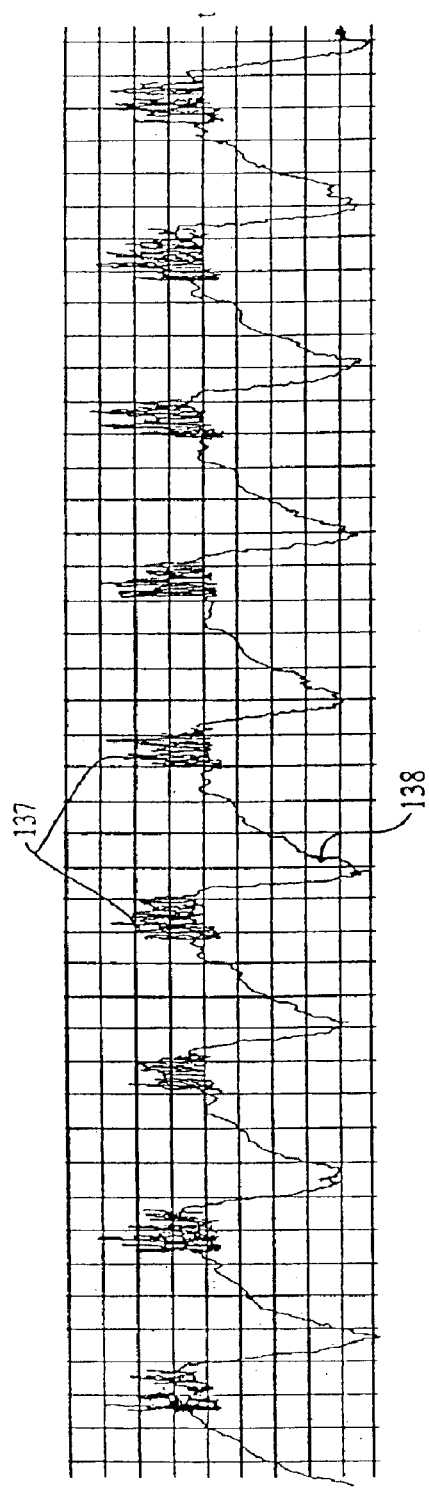
FIG. 11A is a waveform illustrating the uncalibrated flow signal output by the sensor portion of the interface meter in the presence of user snoring.

FIG. 11A illustrates a waveform 138 that corresponds to the uncalibrated analog flow signal 122 output from amplifier 86 in FIG. 8 during inhalation and exhalation. The points in FIG. 11A where waveform 138 crosses the X axis correspond to points where the patient's breathing switches from inspiration to expiration or from expiration to inspiration. Thus, these points can be used as trigger points or reference points for the application of a respiratory therapy, such as an application of positive pressure to the airway or an application of electrical stimulation to the muscles in the patient.

Waveform 138 was generated while the user was asleep and snoring. The rapid signal fluctuations 137 at each apex of inhalation in waveform 138 correspond to the rapid flow variations that take place in the user's respiratory system during snoring. One embodiment of the present invention detects these rapid fluctuations in the raw signal 122 output from the sensor to determine the onset, intensity and duration of snoring. This can be accomplished in a variety of ways, for example, by comparing the rate of change in signal 138 to predetermined thresholds. Because this rapid variation in flow (snore) can be easily detected from waveform 138, the signal from sensor 78, even if not corrected by processor 92, can be used, for example, as a trigger for a therapy intended to relieve such snoring or as a reference point from which therapy is to begin.

Figure 11B:
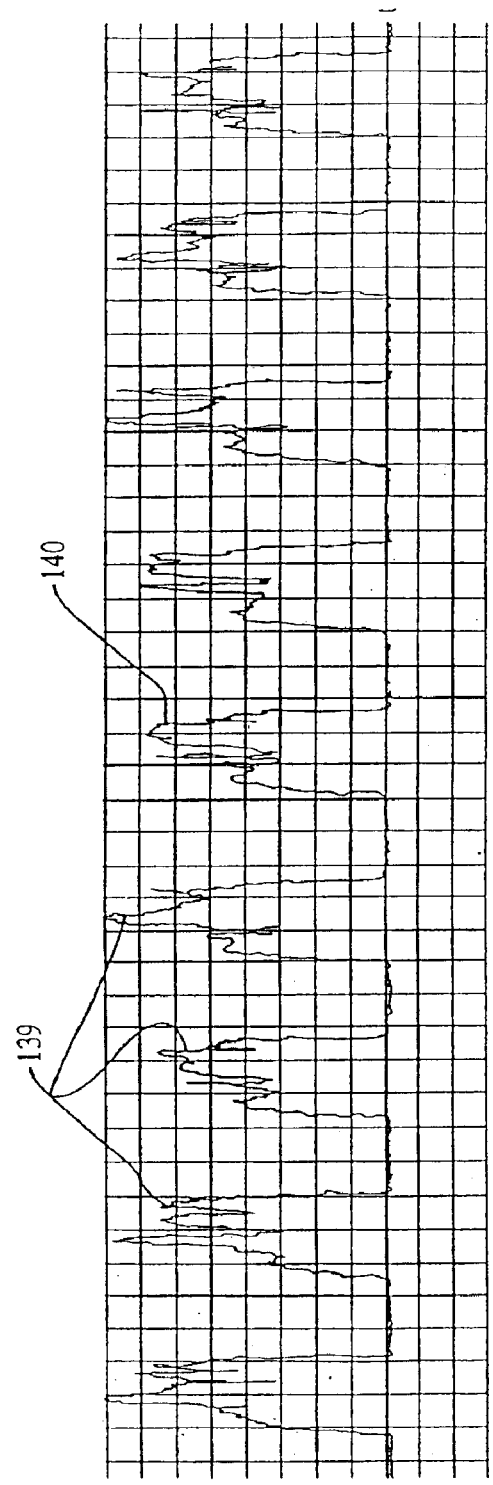
FIG. 11B is a waveform illustrating the calibrated (actual) flow signal output from the interface meter (inhale only) in the presence of snoring.

FIG. 11B illustrates a waveform 140 that corresponds to the signal output from processor 92 based on the signal illustrated in FIG. 11A. In other words, waveform 140 corresponds to the quantitative signal produced by processor 92 based on the raw signal illustrated in FIG. 11A. It should be noted that FIG. 11B illustrates only the inspiration portion of the patient's flow, which is the equivalent of the output at one of terminals 130 and 132 in FIG. 9. As with waveform 138 in FIG. 11A, waveform 140 in FIG. 11B exhibits relatively large and rapid fluctuations 139 during inspiration due to the patient's snoring. These rapid fluctuations can be detected in a variety of fashions, for example, by using a threshold detector, to signal the onset of snoring. It can be appreciated if the processing speed of processor 92 is increased, the rapid fluctuations in the apex of waveform 140 would be even more well defined. In fact, the sensitivity of the present invention is so great that the gas displaced by each individual snore vibration can be determined.

It can be further appreciated that the present invention can determine a wide variety of information based on the output from sensor 78. For example, as noted above, by integrating the quantitative value for flow, which can be done either by processor 92 or using addition components that are either internal or external to the circuit illustrated in FIGS. 5 and 9, the interface meter of the present invention also calculates the volume $V_{TOT}$ of breathing gas entering or exiting the interface. Calculating the volume $V_{TOT}$ can be done in place of or in addition to determining the flow $Q_{TOT}$ of breathing gas passing through the interface. The present invention contemplates providing additional digital-to-analog converters similar to D/A converter 96, additional output devices similar to output device 100, as well as additional output terminals similar to terminals 130 and 132 so that any additional information, such as volume $V_{TOT}$, can be calculated and provided to the user, a third party, or to a data output and/or storage medium.

Knowing the quantitative value for the patient flow makes it possible to determine a number of physical characteristics associated with respiration. This can be done using processor 92 or other circuitry based on the signal output from processor 92 and/or, where possible, the raw signal output from sensor 78. For example, the present invention contemplates using either the raw output of sensor 78 or the flow signal output from processor 92, such as that illustrated in FIG. 10A, to determine the patient's breathing rate, typically in breaths per minute (bpm), minute ventilation, peak expiratory flow, inhalation time, exhalation time, and inhalation to exhalation (I:E) ratio. Also, the present invention contemplates using the volume signal, such as that illustrated in FIG. 10B, to determine the patient's exhalation volume and inhalation volume.

In addition to determining a number of physical characteristics, the patient flow, which is characterized by the raw signal from sensor 78 (FIG. 11A) or the quantitative signal from processor 92 (FIG. 10A), can be used for a variety of purposes. For example, as noted above, the presence, frequency, duration or intensity of rapid fluctuations indicative of snoring can be used to trigger the application of a therapy, such as an airway pneumatic pressure support, to relieve the snoring. The detection of snoring using the patient's flow signal (raw or quantitative) can be used to auto-titrate a pressure support device. Auto-titration is accomplished, for example, by increasing the pressure provided by a pressure support device if the presence or intensity of snoring, or more generally, the presence of any event indicative of the onset of an airway obstruction, is detected, and by decreasing the pressure if such events are not detected for a predetermined period of time. This same principle can be employed with other devices, such as an electrical stimulation device, that is used to relieve the obstruction. Auto-titration can also be accomplished based on the rise time of the flow signal. An increase in rise time can indicate an increase in airway resistance, and hence, the onset of an airway obstruction. This increase in rise time can be detected by the present invention and used to increase the pressure support provided to the patient. The opposite process can be carried out if a decrease in the flow signal rise time is detected.

It is also possible to determine specific characteristics of a patient's snore based on the signal output from sensor 78. For example, the frequency of the snore can be determined from the rapid fluctuations in the flow signal, either from the raw signal output from the sensor or the calibrated, quantitative signal derived from the raw signal. It is known that the frequency of the snore signal can indicate the physical location of the structure or structures in the patient causing the snore. See, for example, the article by S. J. Quinn et al. entitled, "The Differentiation of Snoring Mechanisms Using Sound Analysis," pages 119–123 of Clinical Otolarnynhology, Vol. 21, 1996. Knowing the location of the tissue that is causing the snore is important in determining how to best treat the snore.

Figure 12A:
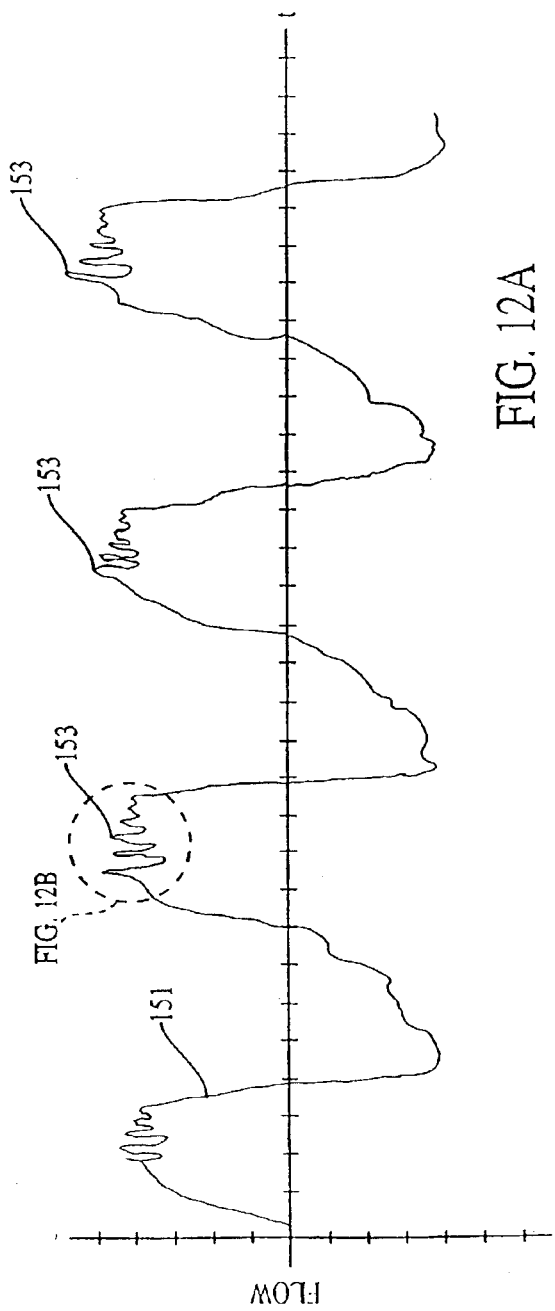
FIG. 12 is a waveform illustrating a flow signal produced by the interface meter of the present invention in the presence of snoring that demonstrates how the present invention is used to analyze patient snoring.
Figure 12B:
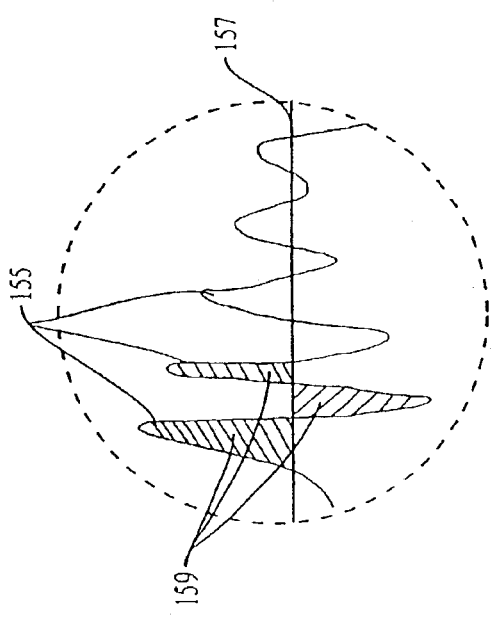

As noted above, the sensitivity of the interface meter of the present invention is great enough that it can detect the amount of gas displaced by each individual snore vibration. For example, FIG. 12 illustrates a flow signal 151 generated by the interface meter of the present invention in the presence of patient snore 153. Snoring 153 appears in flow signal 151 as a series of high frequency oscillations 155 in flow signal 151 that oscillate about a central axis 157. Each oscillation displaces an amount of gas corresponding to the area 159 defined by axis 157 and the curve defining the oscillation.

As noted above, the frequency of a snore can be used to determine the location of the structure or structures in the patient that cause the snore. In a similar manner, the amount of gas displaced by each individual snore vibration can also be used to determine the location of the snore. The amount of gas displaced by each snore vibration is related to the frequency of that snore vibration. For example, the lower the frequency of the snore, the more gas will be displaced by each individual snore vibration. Therefore, by knowing the amount of gas displaced by the individual snore vibrations, the present invention can determine the location of the structure in the patient that is causing the snore. Furthermore, because the present invention accomplishes this function based on the amount of gas displaced by each snore vibration, rather than based on the sound produced by the snore, it is more accurate and less prone to noise than conventional frequency analysis techniques.

Figure 13:
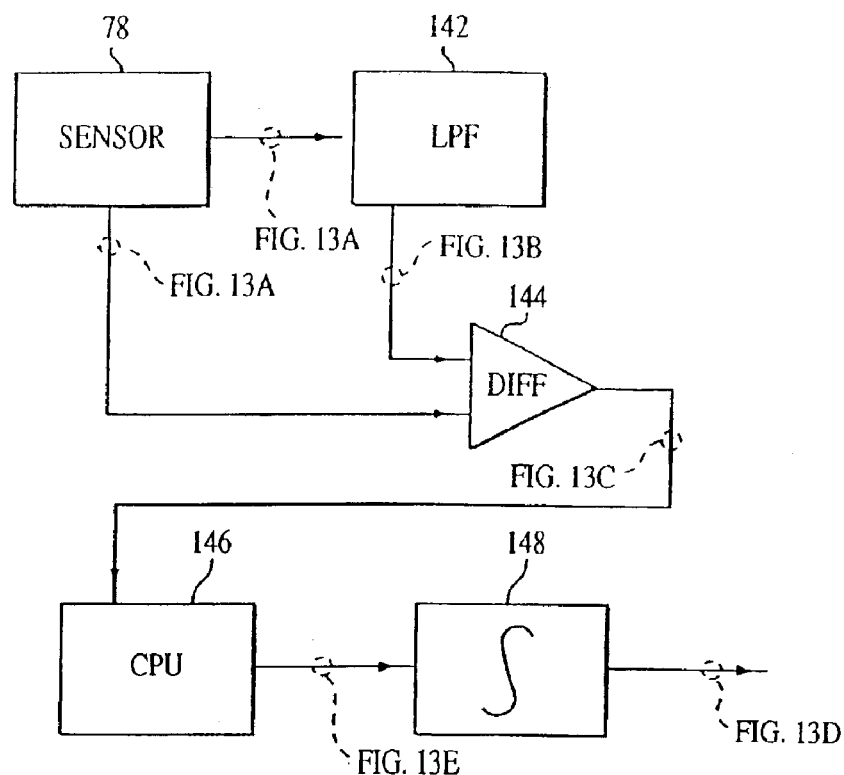
FIG. 13 is a schematic diagram of a circuit used to analyze a patient's snore according to the principles of the present invention.
Figure 13A:
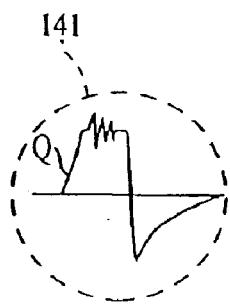
Figure 13B:
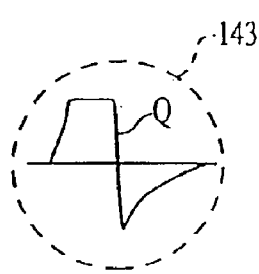
Figure 13C:
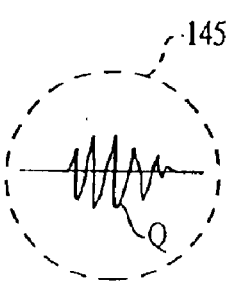
Figure 13D:
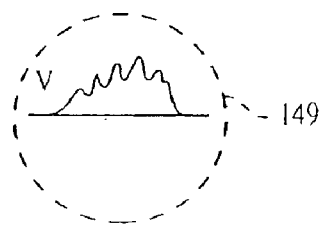
Figure 13E:
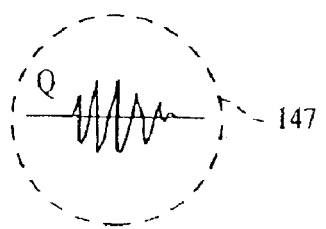

In addition to determining the volume of gas displaced by each vibration in a patient's snore, the present invention also quantitatively determines the volume of the patient's entire snore signal. Quantitatively determining the volume of gas displaced by the patient snore can be accomplished, for example, as shown in FIG. 13. The output 141 of sensor 78 is provided to a low pass filter (LPF) 142 that removes the relatively high frequency snore from the flow signal so that output 143 of low pass filter 142 corresponds to the patient flow without any snore. The flow signals 141 and 143 output from sensor 78 and LPF 142, respectively, are provided to a subtractor circuit 144 so that the output 145 thereof is the raw, uncalibrated analog snore flow signal. Snore flow signal 145 is provided to a processor 146, which uses a look-up table or other technique, to determine the quantitative value of the snore flow 147. Integrating only the positive portion of the snore flow signal 147 in integrator 148 provides a volume accurate snore signal 149, which can be used to analyze the patient's snore. It is to be understood, that only the negative portion of the snore flow signal can be integrated and the same result achieved.

It is to be further understood that other techniques for determining a volume accurate snore signal are contemplated by the present invention. For example, the positive portion of analog signal 145 can be integrated and then software can be used to determine the derivative, which is then converted into a quantitative flow signal to determine a quantitative snore flow signal. This quantitative snore flow signal can then be integrated to provide the volume accurate snore signal. Also, the determination of patient flow, either raw or quantitative, can be made using a conventional flow measuring device.

The information generated by the interface meter of the present invention can also be used in conjunction with other information about the patient's physiology to determine other characteristics of the patient. For example, if a capnometer is used to measure the patient's expired $CO_2$, the flow signal and the capnometer information can be used to determine the volume of $CO_2$ expired by the patient. The volume of $CO_2$ expelled from a patient during exhalation can be determined from the following equation:

$$V_{CO_2} = V_{MIX}\left[\frac{PCO_2}{P_{MIX}}\right]dt,$$

where $V_{MIX}$ is the volume of gas expired by the patient, $PCO_2$ is the pressure of carbon dioxide in the gas expired by the patient, and $P_{MIX}$ is the pressure of the gas expired by the patient. As discussed above, $V_{MIX}$ can be quantitatively determined by the present invention. $PCO_2$ is determined using a capnometer, and $P_{MIX}$ is determined using a conventional barometer.

Similarly, the volume of $CO_2$ expelled from a patient during exhalation can be determined based on the quantitative flow signal using the following equation:

$$V_{CO_2} = \int_{t_1}^{t_2}\left[Q_{Patient}\left(\frac{PCO_2}{P_{MIX}}\right)\right]dt,$$

where: $t_2-t_1$=inhalation period and $Q_{patient}$ is the flow of gas from the patient. This same principle can be used to the measure the volume of other elements expelled by the patient, such as nitrogen, $O_2$, CO, water vapor and any other trace elements that can be detected.

Furthermore, the quantitative flow signal output by the present invention, in combination with other sensing devices, can be used to determine a patient's effective minute ventilation, effective tidal volume, airway dead space, and alveolar volume using conventional techniques. If the patient's arterial $PCO_2$ is also known, further information, such as the physiologic $V_D/V_T$, physiologic dead space, and alveolar dead space can also be determined using conventional techniques.

While the items discussed above describe physiological parameters that are capable of being measured using the present invention, either alone or in combination with other measuring devices, and processes that can be performed or controlled based on the information produced by the present invention, this list is not intended to be exclusive. On the contrary, the present invention can be used to determine any characteristic about a patient that can be derived from the information output by sensor 78 and/or processor 92. Also, the present invention can be used in conjunction with any process that is controlled or requires information of the type produced by the present invention, either directly from the signal output by sensor 78 or processor 92, or indirectly when used combination with other measured physical characteristics.

Although the embodiment of the present invention discussed above has been described for use with a mask-like user interface, it is to be understood that a wide variety of user interfaces, some of which are discussed in greater detail below, can be used in conjunction with the interface meter of the present invention. For example, the patient interface can include, a trachea tube, a mouthpiece or any other device that couples the patient's airway to ambient atmosphere.

Furthermore, the mask serving as a user interface in the embodiment illustrated in FIGS. 4A and 4B can have a wide variety of configurations. For example, user interface 74 can be a nasal mask that covers only the user's nose, a total face mask that encompasses the user's entire face from chin to forehead, a helmet-type mask that encapsulates the user's head. It should also be understood that the term "user interface" is not limited to the mask-like structure illustrated in the figures. Quite the contrary, the "user interface" of the present invention can include structures that attach to the mask-like portion. User interface 72 and tube 82 can be made from any suitable material. In addition, a bacteria filter can be provided anywhere along the length of tube 82. It is preferable to use a bacterial filter and tubing 82 that have a sufficiently low resistance so that a suitable amount of gas flows through sensor 78.

Figure 14:
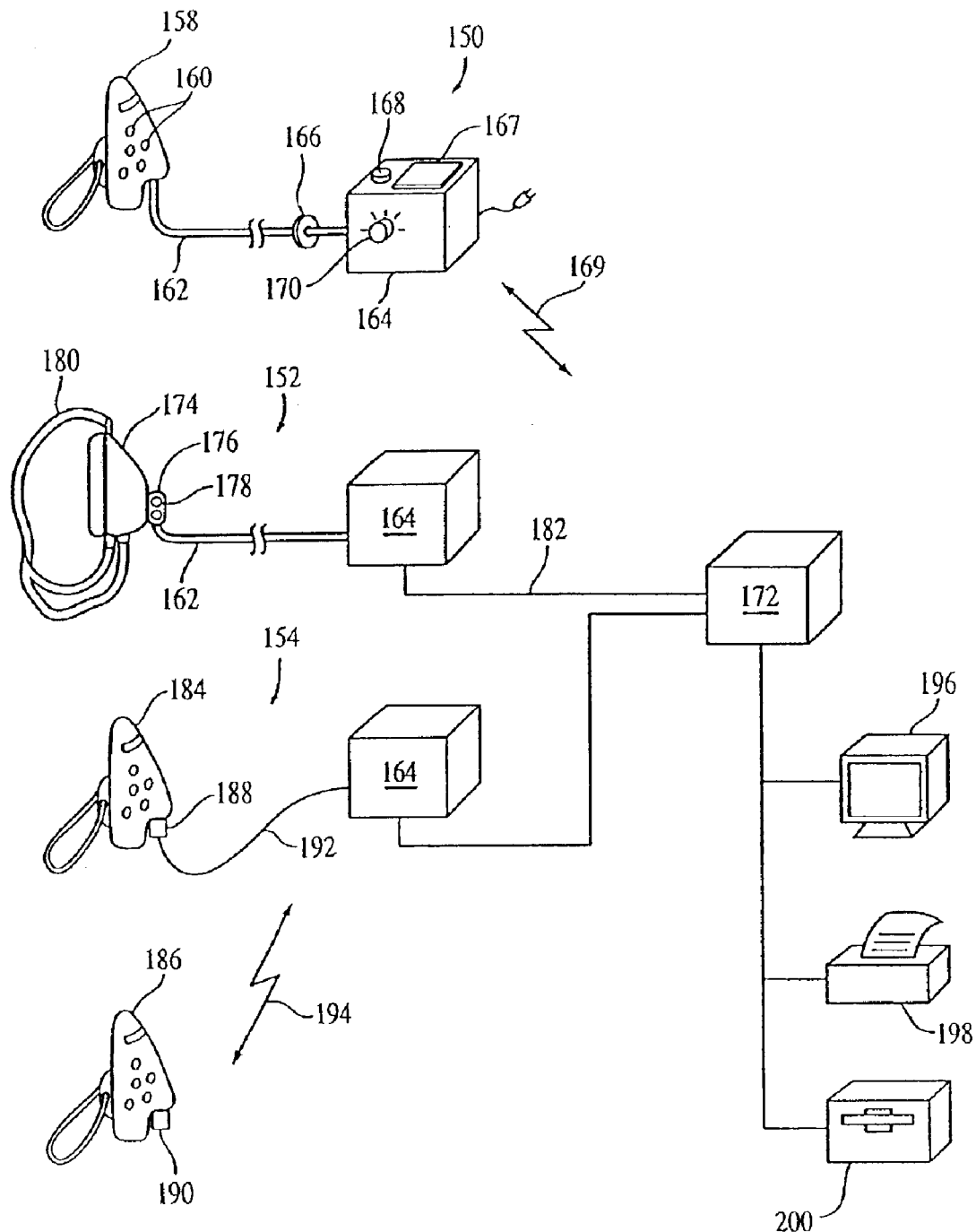
FIG. 14 illustrates various configurations for a first embodiment of the interface meter according to the principles of the present invention.

FIG. 14 illustrates an example of a plurality of interface meters 150, 152, and 154 according to the first embodiment of the present invention. Each interface meter includes a user interface, which in this embodiment is a mask-type interface, a venting element that communicates the interior of the interface to ambient atmosphere and a sensor for measuring a fluid characteristic, such as pressure or flow, resulting from the pressure differential between the interior of the mask and ambient atmosphere created by the venting element.

Interface meter 150, for example, includes a user interface 158 similar to the interface schematically illustrated in FIGS. 4A and 4B. The venting element in interface meter 150 is a plurality of holes 160 provided in user interface 158. A hollow tube 162 having one end selectively coupled to user interface 158 and a second end selectively coupled to a housing 164 communicates the interior of user interface 158 with a sensor (such as sensor 78 in the previous figures) in housing 164. Housing 164 also contains the circuitry illustrated in FIGS. 5 and 9 associated with the sensor. In the illustrated embodiment, a bacteria filter 166 is provided between the first and second ends of tube 162.

Housing 164 includes a display 167 that corresponds to output device 100 in FIGS. 5 and 9 and an on/off activating mechanism 168. Housing 164 also includes a selector 170 so that the user can manually select the type of interface being coupled to housing 164. As discussed above, this enables the processor to use the appropriate look-up table for determining the flow through the interface. Selector 170 and on/off activating mechanism can be any suitable input device for controlling the circuitry and/or processing elements of the present invention. In the illustrated embodiment, interface meter 150 is AC powered. It is to be understood, however, that any suitable power supply, such as batteries, can be used to energize the interface meter.

Interface meter 150 also includes a wireless communication link 169 for communicating with a base unit 172. Any suitable wireless communication system, such as an rf communication link or a modem and land line telephone, cellular, and/or satellite communication system is contemplated by the present invention.

Interface meter 152 is similar to interface meter 150 except that user interface 174 in interface meter 152 does not have holes defined therein. An example of such masks are the nasal mask sold by RESPIRONICS Inc. under the trademark "GOLD SEAL"™ and the full face mask that covers the nose and mouth sold by RESPIRONICS Inc. under the registered trademark "SPECTRUM"®. The venting element that communicates the interior of the interface to ambient atmosphere is an attaching element 176 that selectively couples to a hole defined in user interface 174. Attaching element 176 includes a plurality of holes 178 that communicate the interior of user interface 174 to ambient atmosphere. A headgear 180 attaches the user interface to the patient. As with interface meter 150, a hollow tube 162 couples a sensor in housing 164 to the interior of user interface 174. Interface meter 152 communicates information with base unit 172 via a hard wired link 182.

Interface meter 154 includes a first user interface 184 and a second user interface 186. Unlike interface meters 150 and 152, the interior of user interfaces 184 and 186 communicate directly with a sensor 188 and 190, respectively, that is provided on, in or at the user interface itself, thereby eliminating the hollow tube of the previous embodiments. Sensor 188 in interface meter 154, like sensor 78 in the previous embodiments, measures a fluid characteristic, such as the flow therethrough or the absolute pressure within the mask or the pressure in the mask relative to ambient atmosphere, and outputs a signal via a wire 192 to a processor within housing 164. Sensor 190 performs a similar function except that there is a wireless communication 194 between sensor 190 and housing 164. It is to be further understood that the sensor can be provided within the mask.

Base unit 172 processes the information provided by each interface. For example, the signal from each interface meter can be the raw flow signal from the sensor (sensor 78 in FIG. 5) or the quantitative flow signal from the processor (processor 90 in FIG. 5). Base unit 172 can use these signals, as discussed above, to determine a variety of respiratory characteristics for each patient. Base station 172 can communicate this information, either wirelessly or via wires, to other information processing devices. The illustrated embodiment of the present invention also contemplates providing information from base station 172 to various output/storage devices, such as a display 196, a printer 198, and a storage device 200.

The multiple interface meter system illustrated in FIG. 14 is particularly suited for the hospital or sleep lab environment where multiple patients are monitored by one caregiver. By employing wireless communications between the components of the interface meter, the respiratory characteristics of a patient can be monitored from a remote location, such as the patient's home or while the patient is in transit to a hospital.

Figure 15:
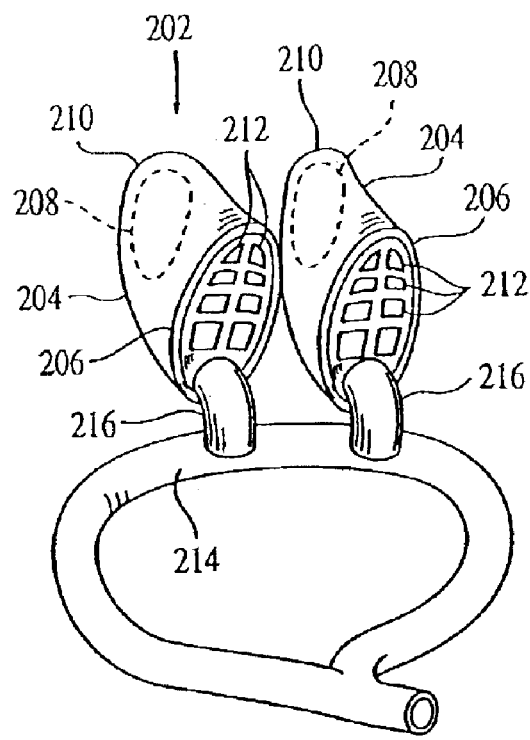
FIG. 15 illustrates a second embodiment of an interface meter according to the principles of the present invention.

While the above embodiment for the interface meter uses a mask-like interface that communicates with the airway of the user, the present invention is not limited to a mask type interface. Quite the contrary, any interface that communicates with the airway of the user is contemplated by the present invention. For example, in a second embodiment of the present invention, as shown in FIG. 15, a pair of nasal prongs 202 replace user interface 72 of FIGS. 4A and 4B. In all other respects, the second embodiment of the present invention and the first embodiment discussed above are the same.

Nasal prongs 202 include protruding portions 204 that insert into the nares of the user. The diameters at each proximal end 206 of protruding portions 202 are sized to seal the nares into which the protruding portion are inserted so that gas does not leak around the periphery of proximal end 206 of protruding portion 204. An opening 208 is defined at a distal end 210 of each protruding portion for communicating an interior portion of the protruding portion with a nasal cavity of the user. At least one vent hole 212 is provided in the proximal end of protruding portions 204. Vent holes 212 perform the same function as holes 76 in the user interface illustrated in FIGS. 4A and 4B. A sensor (not shown) that performs the same function as sensor 78 in FIGS. 4A and 4B is coupled to the interior portion of both protruding portions 204 via a hollow tube 214 and short, connecting tubes 216.

Figure 16:
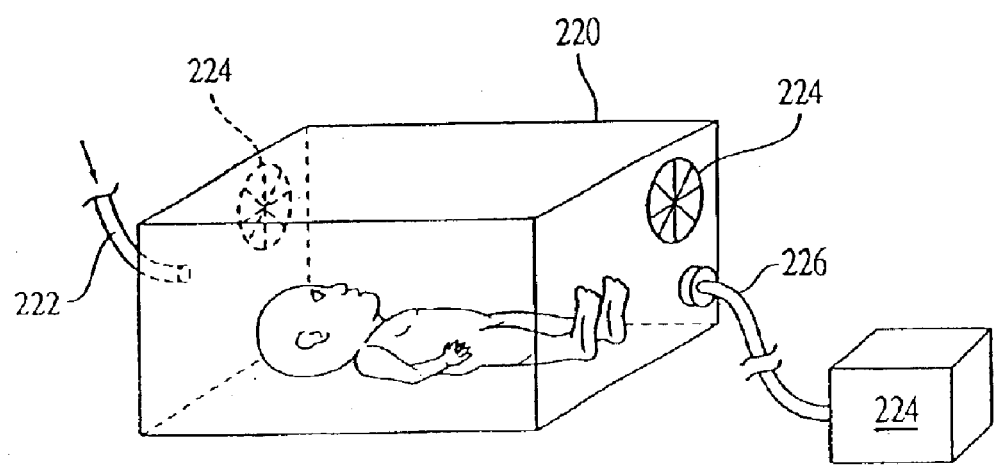
FIG. 16 illustrates a third embodiment of an interface meter according to the principles of the present invention.

FIG. 16 illustrates a third embodiment of an interface meter according to the principles of the present invention. The interface meter in this embodiment includes a incubator chamber 220 as the interface that communicates with the airway of the user. Vent elements 224 are provided in the wall of incubator chamber 200 for communicating the interior portion of the chamber with ambient atmosphere, in the same manner as holes 76 in user interface 72 of FIGS. 4A and 4B. A sampling port is provided in the wall of chamber 220 to communicate a sensor 224 with the interior of the chamber via a hollow tube 226. As with the previous embodiment, tubing 226 can be eliminated and the flow or pressure sensor provided in direct communication with the interior of chamber 220. Sensor 224 corresponds to the circuitry illustrated in FIGS. 5 and 9.

Typically, a breathing gas, such as oxygen or an oxygen mixture, is delivered to the incubator chamber via a gas supply 222. As a result, there is a constant leak from the chamber through vent elements 224. This leak will offset the raw flow or pressure signal from the sensor, as well as the quantitative flow signal output from the processor, so that the flow or pressure signal and quantitative flow signal no longer varies about a zero flow or zero pressure axis. Instead, these signals will fluctuate about a level that corresponds to the leak from the chamber, which corresponds to the flow of breathing gas to the chamber via gas supply 222. In the illustrated embodiment, the processor accounts for this offset caused by the supply of breathing gas so that the output from the processor in sensor 224 is a true representation of the patient's inspiration and expiration. This can be done, for example, by subtracting the leak, once determined, from the quantitative signal output by the processor. Thus, the present invention outputs a quantitative representation of the flow through the chamber even in the presence of a constant supply of gas to the chamber.

Figure 17:
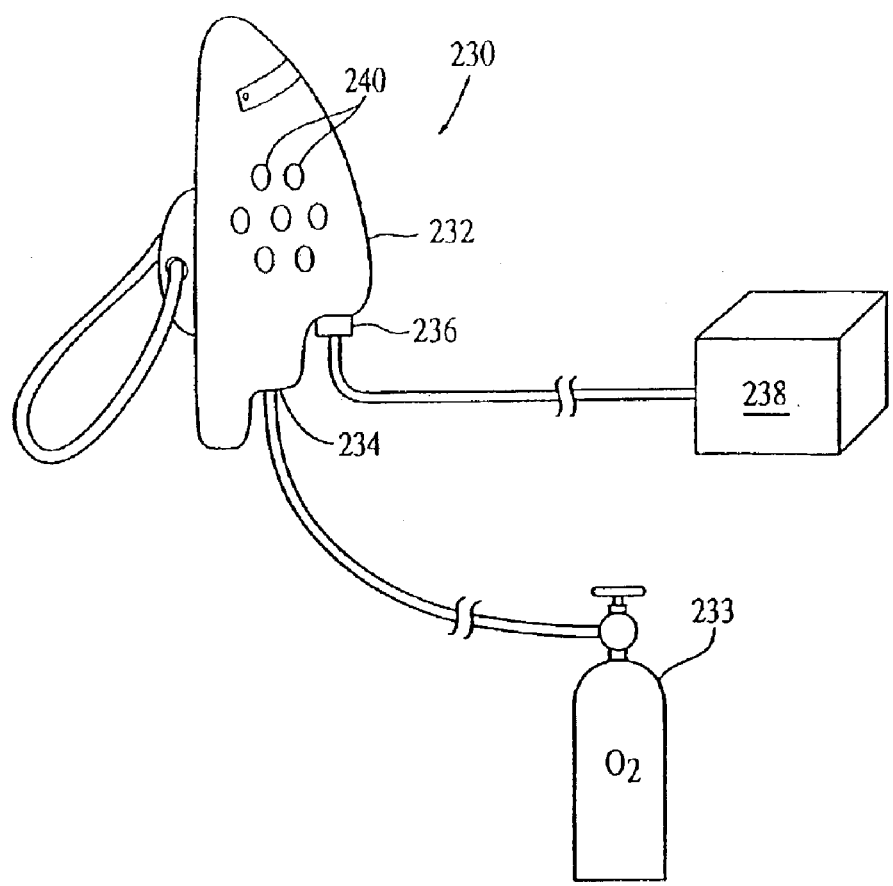
FIG. 17 illustrates a fourth embodiment of an interface meter according to the principles of the present invention.

FIG. 17 illustrates a fourth embodiment of an interface meter 230 according to the principles of the present invention. This embodiment is similar to the embodiments illustrated in FIGS. 4A and 4B except that a breathing gas supply provides a constant supply of breathing gas, such as oxygen or an oxygen mixture, to the interior of mask 232. This embodiment of the present invention is particularly advantageous in that it permits a wide variety of diagnostic information to be garnered from the patient while the patient is being provided with a breathing gas, which is a common medical procedure.

Mask 232 in FIG. 17 includes a first port 234 into which breathing gas from a suitable supply, such as an oxygen tank 233 or oxygen concentrator, is supplied and a second port 236 that communicates a sensor 238 to the interior portion of the mask. It is to be understood that the breathing gas need not be directly provided to the user interface, as shown in FIG. 17. On the contrary, the breathing gas can be provided to the tube connecting sensor 238 to interface 232, thereby avoiding the need to provide two ports in the mask.

In the illustrated embodiment, sensor 238 corresponds to the circuitry illustrated in FIGS. 5 and 9 of the previous embodiment. As with the previous embodiments, a plurality of holes 240 are provided in the mask so that the mask defines a flow element. It is to be understood, however, that any venting system for communicating the interior of the mask with ambient atmosphere, while creating a pressure drop across the flow element, is contemplated by the present invention.

As with the third embodiment illustrated in FIG. 16, the constant supply of a breathing gas to mask 232 produces a substantially continuous leak from the mask. This supply of gas will skew the signals output from the sensor or from the processor so that these signal do not fluctuate about zero during the patient's breathing cycle. Instead, these signals will have a bias that corresponds to the flow of breathing gas into the mask and hence, the leak from the mask. As in the previous embodiment, the present invention compensates for this bias, for example, by subtracting the known leak from the signal output by the sensor or processor. Of course, any other technique for correcting the signals output from the sensor or processor to account for this leak are also contemplated by the present invention. For example, the vertical axis in the waveform diagram for the patient's quantitative flow can be re-labeled so that the bias level caused by the leak is defines as the effective zero flow axis. The flow signal will fluctuate about this effective zero flow axis if a constant supply of gas is delivered to the mask.

Figure 18:
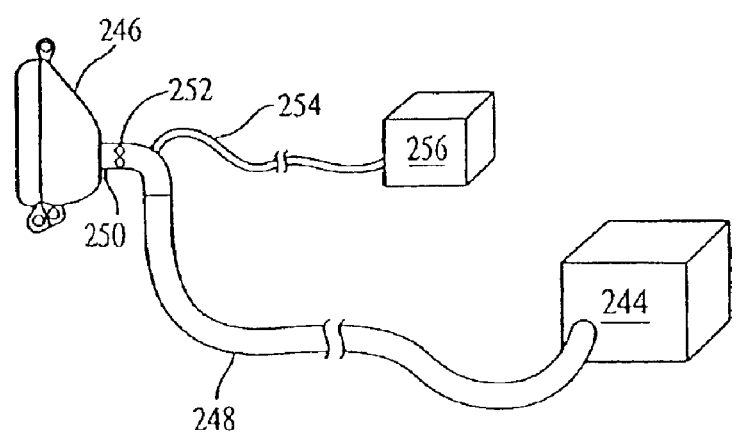
FIG. 18 illustrates a fifth embodiment of an interface meter according to the principles of the present invention.

FIG. 18 illustrates a fifth embodiment of an interface meter according to the principles of the present invention. This embodiment is similar to the embodiment discussed above with respect to FIG. 17 except that a positive pressure device 244 supplies a breathing gas to an interface 246 via a breathing circuit 248. In the illustrated embodiment, interface 246 is a mask interface that covers the user's nose or the user's nose and mouth. There are no holes in the mask to serve as a venting element. Instead, an adapter device 250 is coupled to the mask. Adapter device 250 attaches an end of breathing circuit 248 to mask 246. Adapter device 250 also includes at least one hole 252, which can have a variety of configurations, that communicates the interior portion of mask 246 to the ambient atmosphere. A hollow tube 254 is coupled to a port defined in adapter device 250 to communicate an a sensor 256 with the interior of mask 246. Sensor 256 performs the same function as the circuit illustrated in FIGS. 5 and 9. It is to be understood, however, that sensor 256 can be coupled to other portions of the mask a breathing circuit. For example, sensor 256 can be coupled directly to a pick-off port defined in mask 246 or can be provided along breathing circuit 248, so long as sensor 256 measures a fluid characteristic associated with the pressure differential caused by venting the interior of the mask to ambient atmosphere.

The present invention also contemplates that holes 252 can be removed from the interface and/or breathing circuit so that there is no venting element between the positive pressure device and the patient. Instead, the gas inlet to the positive pressure device serves as the primary venting element, i.e., gas inlet/out, for the patient circuit. During inhalation, the patient's inhalation and the pressure provided by the positive pressure provide breathing gas to the patient. During exhalation, the force of the patient's expiration causes gas to be backed up into the positive pressure device and out of the gas inlet provided thereon.

As with the third and fourth embodiments illustrated in FIGS. 16 and 17, the constant supply of a breathing gas to mask 246 produces a substantially continuous leak from the mask via holes 252. As in the previous embodiments, the present invention compensates for the bias caused by this supply of gas, for example, by subtracting the known leak from the signal output by the sensor or processor. If bi-level pressure or variable pressure is provided by positive pressure device 244, compensations techniques such as those discussed above, can be employed to correct for the bias imposed by the variable pressure.

Figure 19:
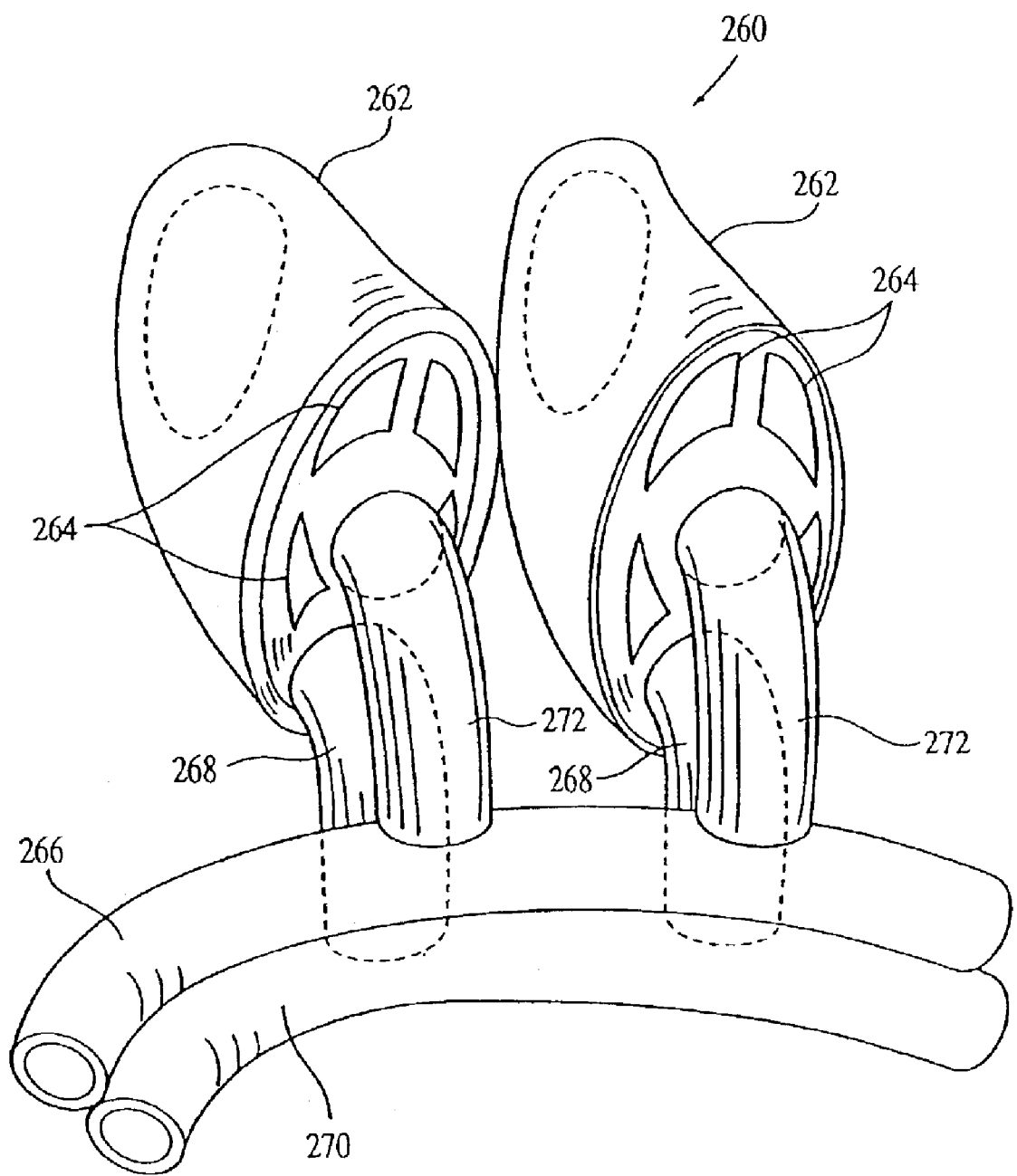
FIG. 19 illustrates a sixth embodiment of an interface meter according to the principles of the present invention.

Although FIGS. 17 and 18 illustrate providing a supply of breathing gas to a mask-type patient interface, it is to be understood that a breathing gas, such as oxygen, can be supplied to other types of patient interfaces, in addition to the incubation chamber illustrated in FIG. 15, according to the principles of the present invention. FIG. 19, for example, illustrates a nasal prong patient interface that is similar to that illustrated in FIG. 15, except that nasal prong interface 260 in FIG. 19 includes a supply of oxygen to the patient. In all other respects, the sixth embodiment of the present invention and the embodiment illustrated in FIG. 14 are the same.

In the illustrated embodiment, nasal prongs 260 include protruding portions 262 that insert into the nares of the user and opens are provided in each end of the protruding portions. The proximal end of protruding portions 262 include at least one vent hole 264 that perform the same function as vent holes 212 in the nasal cannula illustrated in FIG. 15. A sensor (not shown) that performs the same function as sensor 78 in FIGS. 4A and 4B is coupled to the interior portion of both protruding portions 262 via a first hollow tube 266 and short, connecting tubes 268. A breathing gas, such as oxygen, is provided to the interior of protruding portions 262 via a second hollow tube 270 and short, connecting tubes 272. The constant supply of breathing gas to nasal prongs 262 produces a substantially continuous leak from the protruding portions holes 264. As in the previous embodiments, the present invention compensates for the bias caused by this supply of gas, for example, by subtracting the known leak from the signal output by the sensor or processor.

The present invention also contemplates that a breathing gas can be provided to the tubing connecting the nasal prong interface to the sensor. This embodiment is advantageous in that it eliminates that need for two hollow tubes and two connecting tubes to be connected to each protruding portion of the nasal prong interface.

Figure 20:
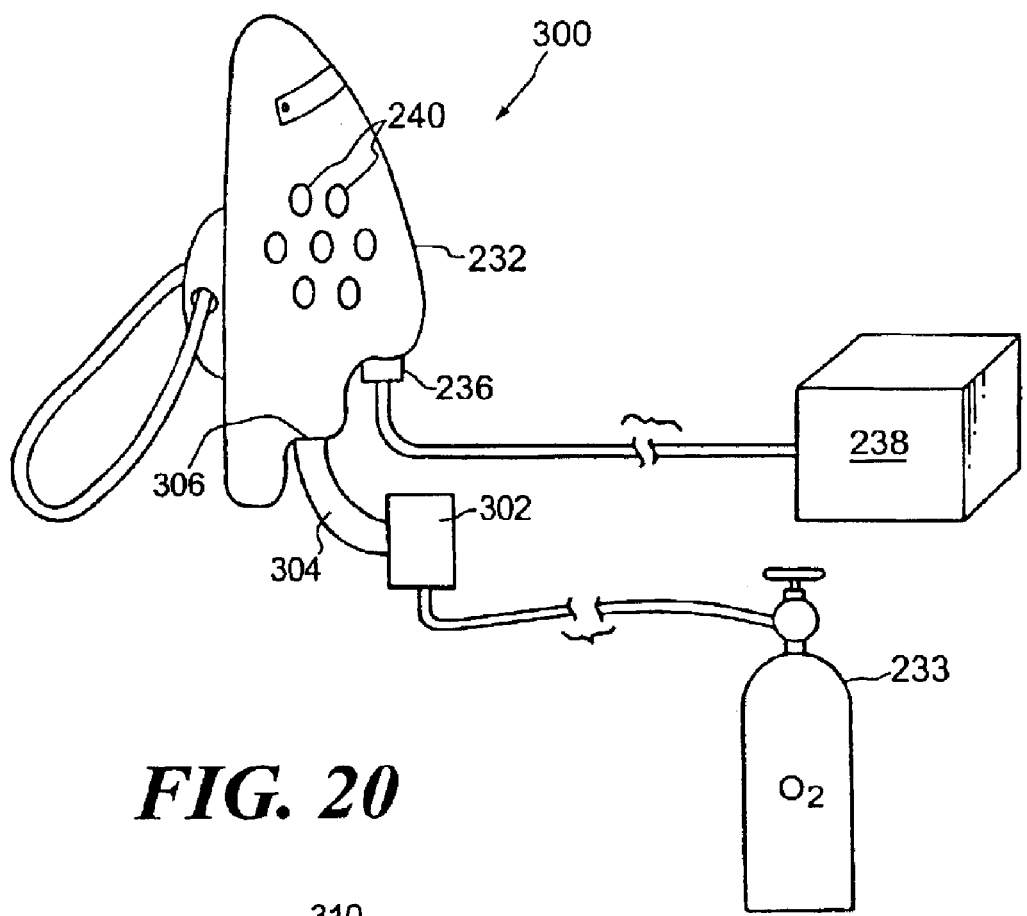
FIG. 20 illustrates a seventh embodiment of an interface meter according to the principles of the present invention.

A still further embodiment of interface meter 300 of the present invention is shown in FIG. 20. The interface meter of this embodiment is substantially similar to that shown in FIG. 17, except that a nebulizer or a medication delivery device 302 is provided in addition to the supply of breathing gas or oxygen. This embodiment allows a supply of aerosolized medication or other therapeutic or medicated gas to be delivered to the patient via a relatively large bore conduit 304 connected to patient interface device 232 at port 306. The internal cross-sectional area of conduit 304 and port 306 should be larger than that of a standard oxygen cannula to allow the aerosolized medication to be delivered efficiently to the patient.

In the embodiments of the interface meter discussed above, a single sensor, such as sensor 78, 238 or 256 is provided for measuring the total flow of gas into and out of the patient. The present further contemplates measuring the flow of gas into and out of each separate orifice of the patient. This allows a caregiver a means to accurately diagnose where an obstruction is occurring, for example.

Figure 21:
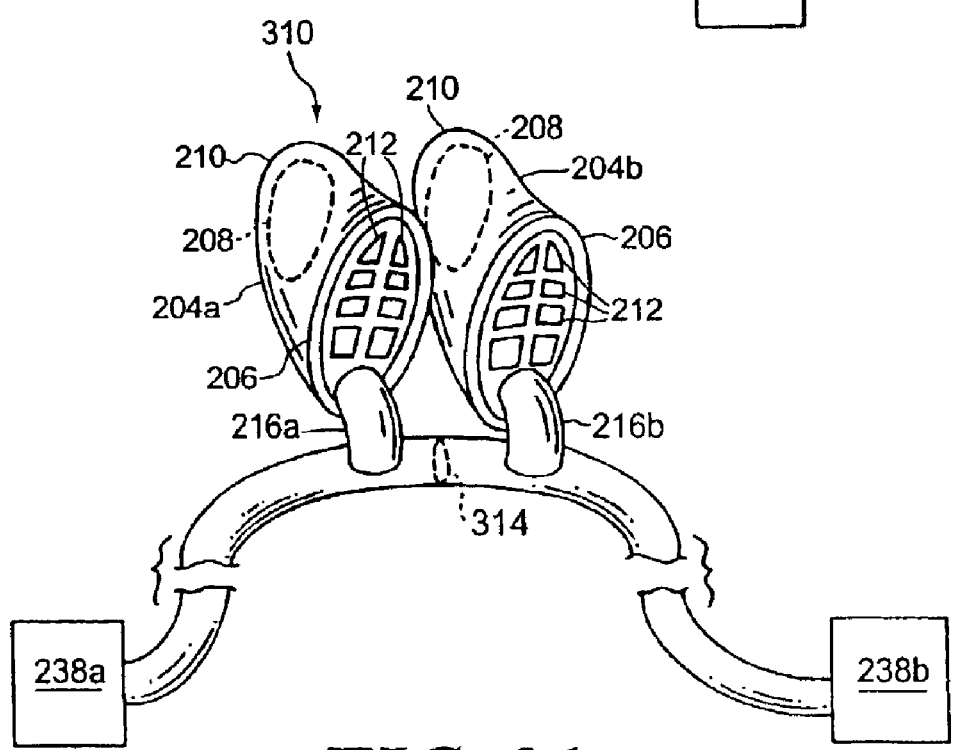
FIG. 21 illustrates an eight embodiment of an interface meter according to the principles of the present invention.

FIG. 21 illustrates a nasal prong 310 in which the flow of gas into and out of the left and right nostril are measured independently. Nasal prong 310 is generally the same as nasal prong 202 of FIG. 15, except that each protruding portion 204a and 204b, associated with the right and left nostrils, respectively, are connected to separate sensors 238a and 238b via separate connecting tubes 216a and 216b. In the illustrated embodiment, a blockage 314 isolated connecting tubes 216a and 216b from one another. It should be noted that this same technique of independently measuring the flow of gas at the right and left nostril is applicable to the nasal prong embodiment shown in FIG. 19.

Figure 22:
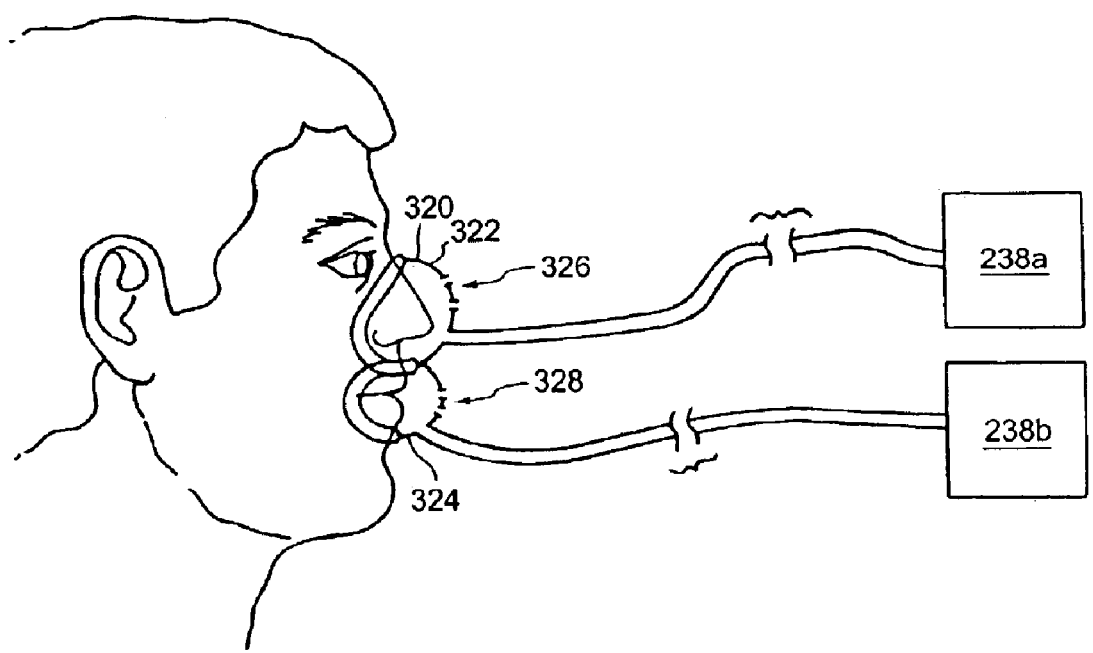
FIG. 22 illustrates a ninth embodiment of an interface meter according to the principles of the present invention.

FIG. 22 illustrates a patient interface device 320 with independent nasal and mouth flow measurement capabilities. To achieve these independent flow measurements, interface 320 includes a first portion 322 that captures the flow of gas at the nose, and a section portion 324 that captures the flow of gas at the mouth. Each portion 322 and 324 includes at least one vent port 326 and 328 that serves the same function as holes 76. The interior of first portion 322 and section portion 324 are in fluid communication with separate sensors 238a and 238b, respectively, to make independent flow or volume measurements in the manner discussed above. Those skilled in the art will appreciated that any number of configurations for interface device 320 are possible so long as the flow of gas at the mouth and nose are insolated and measured independently.

Figure 23A:
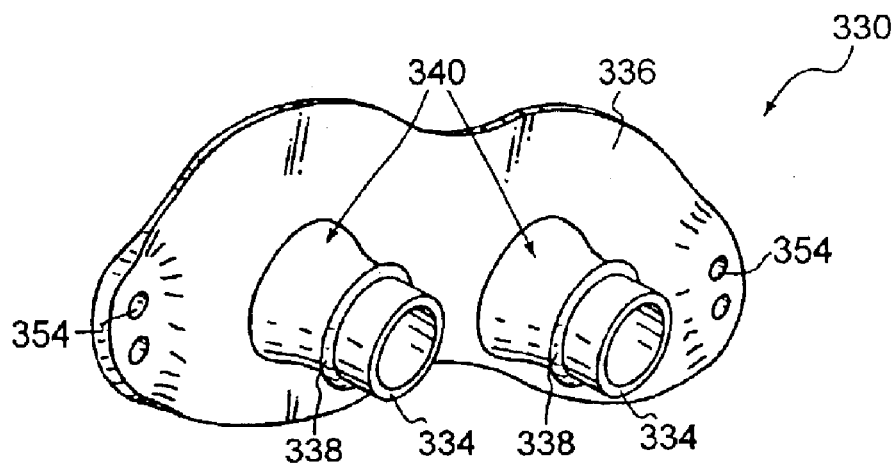
FIG. 23A is a rear perspective view.
Figure 23B:
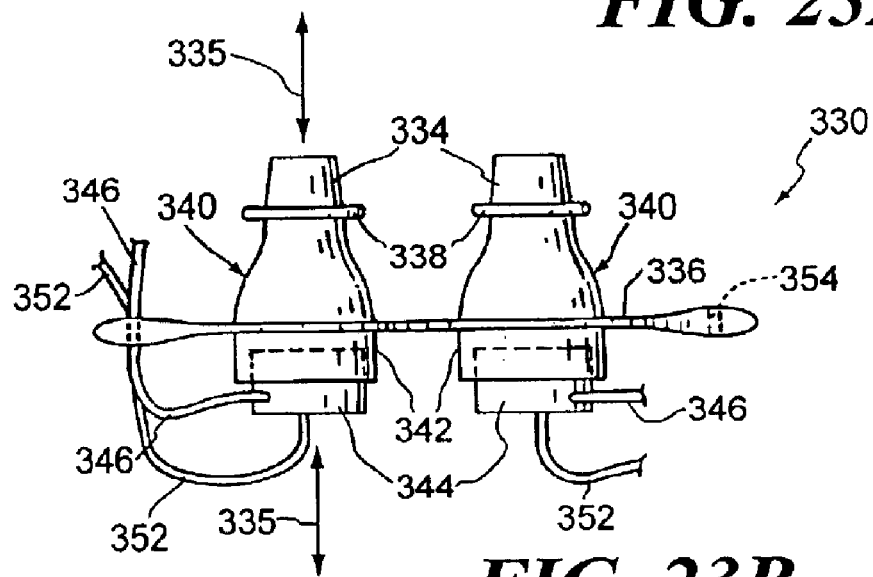
FIG. 23B is a top view.
Figure 23C:
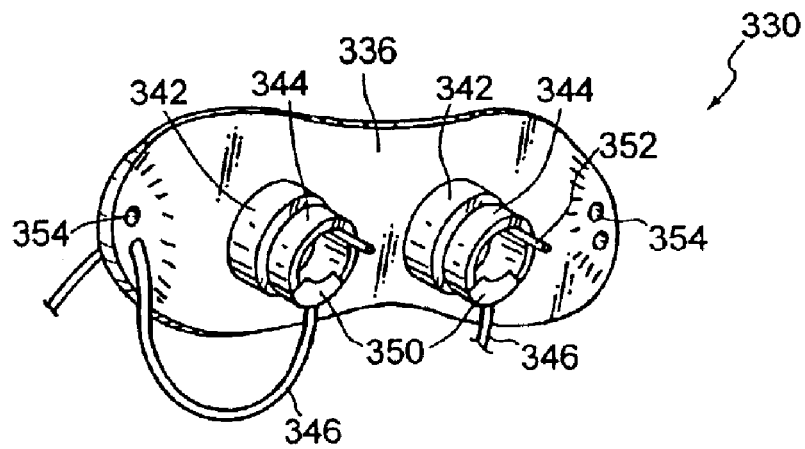
FIG. 23C is a front perspective view of a tenth embodiment of an interface meter according to the principles of the present invention.

FIGS. 23A–23C illustrate a nasal prong patient interface 330 according to a further embodiment of the present invention. Nasal prongs 330, like nasal prongs 202 of FIG. 15, includes a pair of protruding portions 334 supported by a base member 336. In a preferred embodiment of the present invention, protruding portions 334 are integral with base member 336 and all are formed from a relatively flexible and biocompatible material. Protruding portions 334 insert into the patient's nares and seal the nares so that all gas passing through the each nostril must pass through the protruding portions, as indicated by arrows 335. Flanges 338 are provided to facilitate this sealing function so that no gas escape around the protruding portions. Flanges 338 can have any size and shape or multiple flanges can be provided to achieve this function.

In the illustrated exemplary embodiment, the outside diameter of each protruding portion increases as the distance toward base member 336 decreases. This increase in diameter is identified by numeral 340 in FIGS. 23A and 23B. The increase in diameter serves to seal the protruding portions against the nostrils to prevent gas from leaking around the patient interface.

A pair of flow element portions 342 are provided on the side of base member 336 opposite the side that protruding portions 334 are located. In a preferred embodiment of the present invention, flow element portions 342 are integral with base member 336. A pair of rigid rings 344 are provided in flow element portions 342. Rings 344 provide a mounting structure for pressure/flow tubes 346 that are used to measuring the pressure or flow of gas passing through each channel between the patient and ambient atmosphere. More specifically, a small hole is defined in each ring and tube 346 is connected to each hole. In this manner, the pressure or flow can be measured as done by tube 82 and sensor 78 in FIGS. 4A and 4B.

In the illustrated embodiment, a relatively small lip 350 is provided along an edge of each ring 344 to produce the necessary pressure drop along each channel for so that the flow or pressure can be measured. Preferably the hole in each ring for pressure or flow measurement purposes is provided adjacent to each lip because this is the location where the pressure differential in the channel is maximized.

An optional supplemental gas delivery conduit 352 is shown attached to each ring. This conduit is used, for example, to deliver oxygen to the nasal passages of the patient in the same manner tubes 270 and 272 deliver supplemental oxygen in the embodiment shown in FIG. 19.

In this embodiment, holes 354 are provided on each edge of base member 336. Holes 354 help contain tubes 346 and 352 and prevent them from interfering with other medical equipment or from being distracting or annoying to the patient. Of course, the present invention contemplates any number of techniques for securing the pressure/flow sensing tube and gas delivery tubes to the patient.

Rings 344 are preferably rigid so that the cross sectional area through the rings does not change, thereby ensuring flow/pressure measuring accuracy. Because rings 344 are removable from flow element portions 342 of patient interface 330, the individual structures can be easily cleaned or components replaced as needed. It is to be understood, however, that rings 344 can be integral with flow element portions 342. Furthermore, the present invention contemplates that separate sensors can be associated with each airflow channel so that the flow of gas through each nostril can be measured independent, as discussed above.

Although the invention has been described in detail for the purpose of illustration based on what is currently considered to be the most practical and preferred embodiments, it is to be understood that such detail is solely for that purpose and that the invention is not limited to the disclosed embodiments, but on the contrary, is intended to cover modifications and equivalent arrangements that are within the spirit and scope of the appended claims. For example, while processor 92 and 146 have be described in terms of an integrated circuit that is carries out a predetermined program, it is to be understood that these functions could be accomplished using hardwired circuit elements.

What is claimed is:

1. A patient monitoring apparatus, comprising:
    a patient interface adapted to be located at an airway of a patient such that substantially all gas passing through the airway passes through the patient interface;
    at least one vent element associated with the patient interface to communicate a portion of gas passing through the patient interface with an ambient atmosphere, thereby creating a pressure differential between a pressure within the patient interface and a pressure of ambient atmosphere;
    a sensor operatively coupled to the patient interface and adapted to measure a fluid characteristic resulting from the pressure differential, wherein the sensor outputs a signal indicative of the fluid characteristic;
    an oxygen source;
    a conduit connecting the oxygen source to the patient interface to provide a flow of oxygen from the oxygen source to the airway of such a patient; and
    a processing unit, receiving the signal, and accounting for an offset in the signal caused by the flow of oxygen to the patient interface.

2. The apparatus of claim 1, wherein the processing unit determines a quantitative value for a physiological characteristic of such a patient based on the signal.

3. The apparatus of claim 1, wherein the patient interface is a nasal cannula or a mask.

4. The apparatus of claim 1, wherein the sensor is 1) an airflow sensor, and the fluid characteristic measured by the sensor is a rate of flow of gas passing through the sensor, or 2) a pressure sensor, and the fluid characteristic measured by the sensor is a pressure within the patient interface.

5. The apparatus of claim 1, wherein the oxygen source is an oxygen storage system or an oxygen generating system.

6. A patient monitoring method, comprising the steps of:
    locating a patient interface at an airway of a patient such that substantially all gas passing through the airway passes through the patient interface, wherein the patient interface includes at least one vent element associated therewith that communicates a portion of gas passing through the patient interface with an ambient atmosphere, thereby creating a pressure differential between a pressure within the patient interface and a pressure of ambient atmosphere;

communicating a flow of oxygen from an oxygen source to the airway of such a patient;

passing a flow of gas from the patient interface to ambient atmosphere across the vent element to create the pressure differential;

measuring a fluid characteristic resulting from the pressure differential; and accounting for an offset a measurement of the fluid characteristic caused by the flow of oxygen to the patient interface.

7. The method of claim 6, further comprising determining a quantitative value for a physiological characteristic of such a patient based on the fluid characteristic.

8. The method of claim 6, wherein the patient interface is a nasal cannula or a mask.

9. The method of claim 6, wherein the measuring step is accomplished using 1) an airflow sensor, and the fluid characteristic is a rate of flow of gas through the airflow sensor between the patient interface and ambient atmosphere, or 2) a pressure sensor, and the fluid characteristic is a pressure in or near the patient interface.

10. The method of claim 6, wherein 1) the oxygen source is an oxygen storage system and communicating a flow of oxygen from the oxygen source includes depleting oxygen from the oxygen storage system, or 2) the oxygen source is an oxygen generating system and communicating a flow of oxygen from the oxygen source includes generating oxygen via the oxygen generating system.

* * * * *